(12) United States Patent
Roe

(10) Patent No.: US 9,186,344 B2
(45) Date of Patent: *Nov. 17, 2015

(54) GLYCOGEN OR POLYSACCHARIDE STORAGE DISEASE TREATMENT METHOD

(71) Applicant: Baylor Research Institute, Dallas, TX (US)

(72) Inventor: Charles R. Roe, Rockwell, TX (US)

(73) Assignee: BAYLOR RESEARCH INSTITUTE, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/214,317

(22) Filed: Mar. 14, 2014

(65) Prior Publication Data

US 2014/0288175 A1 Sep. 25, 2014

Related U.S. Application Data

(60) Continuation of application No. 13/343,578, filed on Jan. 4, 2012, now Pat. No. 8,697,748, which is a division of application No. 11/172,693, filed on Jul. 1, 2005, now Pat. No. 8,106,093.

(60) Provisional application No. 60/585,502, filed on Jul. 2, 2004.

(51) Int. Cl.

| | | |
|---|---|---|
| *A61K 31/23* | (2006.01) | |
| *A61K 31/22* | (2006.01) | |
| *A61K 31/19* | (2006.01) | |
| *A61K 31/225* | (2006.01) | |
| *A61K 31/202* | (2006.01) | |
| *A61K 31/20* | (2006.01) | |

(52) U.S. Cl.
CPC ............... *A61K 31/225* (2013.01); *A61K 31/19* (2013.01); *A61K 31/202* (2013.01); *A61K 31/22* (2013.01); *A61K 31/20* (2013.01); *A61K 31/23* (2013.01)

(58) Field of Classification Search
CPC ............................. A61K 31/23; A61K 31/20
USPC .................. 514/552, 547, 558, 560
See application file for complete search history.

(56) References Cited

U.S. PATENT DOCUMENTS

| | | | |
|---|---|---|---|
| 3,697,563 A | 10/1972 | Garzia | |
| 4,042,684 A | 8/1977 | Kahm | |
| 4,753,963 A | 6/1988 | Jandacek et al. | |
| 4,871,557 A | 10/1989 | Linscott | |
| 4,981,687 A | 1/1991 | Fregly et al. | |
| 5,153,221 A | 10/1992 | Revici | |
| 5,908,631 A | 6/1999 | Arnaud et al. | |
| 5,968,982 A | 10/1999 | Voss et al. | |
| 6,225,347 B1 | 5/2001 | Buchmann et al. | |
| 6,723,358 B1 | 4/2004 | Van Lengerich | |
| 6,740,679 B1 | 5/2004 | Roe | |
| 6,746,698 B2 | 6/2004 | Freeman | |
| 6,777,396 B2 | 8/2004 | Shinzato et al. | |
| 7,754,764 B2 | 7/2010 | Roe | |
| 8,106,093 B2 | 1/2012 | Roe | |
| 8,507,558 B2 * | 8/2013 | Roe | 514/560 |
| 8,697,748 B2 * | 4/2014 | Roe | 514/552 |
| 2011/0306663 A1 | 12/2011 | Schiffmann et al. | |

FOREIGN PATENT DOCUMENTS

| | | |
|---|---|---|
| EP | 0530861 | 3/1993 |
| EP | 0801944 | 10/1997 |
| EP | 0861657 | 9/1998 |
| JP | 52-015834 | 2/1977 |
| WO | WO 96/15784 | 5/1996 |
| WO | WO 00/45649 | 8/2000 |
| WO | WO 2006/014353 | 2/2006 |

OTHER PUBLICATIONS

Office Action for Canadian Application No. 2,573,054, mailed Aug. 27, 2010.
Office Action for Canadian Application No. 2,573,054, mailed Dec. 16, 2009.
Office Action for European Application No. 05764401.5, mailed Jul. 10, 2013.
Supplementary European Search Report for European Application No. 05764401.5, mailed Sep. 3, 2012.
International Search Report and Written Opinion for International Application No. PCT/US2005/023524, mailed Feb. 3, 2006.
Office Action for Canadian Application No. 2,784,420, dated May 16, 2013.
Office Action for Canadian Application No. 2,784,585, mailed Dec. 19, 2013.
Anderson et al., "Glucogenic and ketogenic capacities of lard, safflower oil, and triundecanoin in fasting rats," J. Nutri., 105:185-189 (1975).
Bach et al., "Medium-chain triglycerides: an update," Am. J. Clin. Nutri., 36:950-962 (1982).
Bohles et al., "The influence of intravenous medium- and long-chain triglycerides and carnitine on the excretion of dicarboxylic acids," Journal of Parenteral and Enteral Nutrition, 11(1):46-48 (1987).

(Continued)

*Primary Examiner* — Kevin E Weddington
(74) *Attorney, Agent, or Firm* — Cooley LLP

(57) ABSTRACT

A method for treating glycogen storage disease by administering an effective amount of a composition that includes ketogenic odd carbon fatty acids that ameliorate the symptoms of these diseases.

26 Claims, 9 Drawing Sheets

(56) References Cited

OTHER PUBLICATIONS

Boyer et al., "Hepatic metabolism of 1-14C margaric acids," Lipids, 4(6):615-617 (1970).
Carey, P. E. et al., "Direct Assessment of Muscle Glycogen Storage After Mixed Meals in Normal and Type 2 Diabetic Subjects," Am. J. Physiol. Endocrinol. Metab., 284:E688-E694 (2003).
Evers, S., "AAEP 2002: A Review of the Diagnosis and Treatment of Rhabdomyolysis in Foals," http://www.thehorse.com, Article #4139 (Feb. 2003).
Firshman, A. M. et al., "Epidemiologic Characteristics and Management of Polysaccharide Storage Myopathy in Quarter Horses," Am. J. Vet. Res., 64(10):1319-1327 (2003).
Gray, L., "Polysaccharide Storage Myopathy (Glycogen Storage Disease)," Horse Previews, 2 pages (Jul. 2002).
Greene, H. L. et al., "Hyperlipidemia and fatty acid composition in patients treated for type IA glycogen storage disease," Journal of Pediatrics, 119(3):398-403 (1991).
Huerta-Alardin, A. L. et al., "Bench-to-bedside review: Rhabdomyolysis—an overview for clinicians," Critical Care, 9(2):158-169 (2005).
Ibrahim, J. et al., "Glycogen-Storage Disease Type II," [online], eMedicine, http://www.emedicine.com/PED/topic1866.htm (2003).
Iwama et al., "Hypertrophic Cardiomyopathy Complicated with Acute Myocardial Infarction due to Coronary Embolism," Internal Medicine, 36:613-617 (1997).
Jones et al., "Fat Malabsorption in Congestive Cardiac Failure," British Med. J., 1(5235):1276-1278 (1961).
Kaminski, M. Jr. et al., "AIDS wasting syndrome as an entero-metabolic disorder: the gut hypothesis," Alt. Med. Rev., 3(1):40-53 (1998).
Kerner et al., "Genetic Disorders of Carnitine Metabolism and Their Nutritional Management," Annual Rev. Nutri., 18:179-206 (1998).
Lin et al., "Acetate represents a major product of heptanoate and octanoate beta-oxidation in hepatocytes isolated from neonatal piglets," Biochem J., 318:235-240 (1996).
Linseisen, J. et al., "Odd-numbered medium-chain triglycerids (trinonanoin) in total parenteral nutrition: effects on parameters of fat metabolism in rabbits", Journal of Parenteral and Enteral Nutrition, 17(6):522-528 (1993).
McKenzie, E. C. et al., "Effect of Dietary Starch, Fat, and Bicarbonate Content on Exercise Responses and Serum Creatine Kinase Activity in Eqine Recurrent Exertional Rhabdomyolysis," J. Vet. Intern. Med., 17:693-701 (2003).
Miller et al., "The Pig as a Model for Human Nutrition," Annual Rev. Nutri., 7:361-382 (1987).
Niezen-Koning et al., "A patient with lethal cardiomyopathy and a carnitine-acylcarnitine translocase deficiency," J. Inher. Melab. Dis., 18:230-232 (1995).
Odle et al., "Utilization of medium-chain triglycerides by neotatal piglets: II. Effects of even- and odd-chain triglyceride consumption over the first 2 days of life on blood metabolites and urinary nitrogen excretion," J. Anim. Sci., 67:3340-3351 (1989).
Odle et al, "Utilization of medium-chain triglycerides by neonatal piglets: chain length of even- and odd-carbon fatty acids and apparent digestion/absorption and hepatic metabolism," J. Nutri., 121:605-614 (1991).
Odle et al., "Evaluation of [1-14C]-medium chain fatty acid oxidation by neonatal piglets using continuous-infusion radiotracer kinetic methodology," J. Nutri., 122:2183-2189 (1992).
Odle et al., "Emulsification and fatty acid chain length affect the kinetics of [14C]-medium-chain length triacylglycerol utilization by neonatal piglets," J. Nutri., 124:84-93 (1994).
Odle et al., "New insights into the utilization of medium-chain triglycerides by the neonate: observations from a piglet model," J. Nutri., 127:1061-1067 (1997).
Pi-Sunyer, F. X., "Rats enriched with odd-carbon fatty acids: effect of prolonged starvation on liver glycogen and serum lipids, glucose and insulin," Diabetes, 20(4):200-205 (1971).
Reynolds, J. A., "Feeding Fats and Oils to Horses," [online], Alliance Nutrition Equine, http://www.admani.com/AllianceEquine/TechBulletins/FeedingFatsAndOilsToHo-rses.htm (2004).
Rice, G. M. et al., "Metabolic Disorders in Pediatric Neurology," Neurology, 9(Part 2):1-15 (2005).
Roe, C. R. et al., "Treatment of cardiomyopathy and rhabdomyolysis in long-chain fat oxidation disorders using an anaplerotic odd-chain triglyceride," Journal of Clinical Investigation, 110(2):259-269 (Jul. 2002).
Roughton, "A synthetic alternative to fermented eggs as a canid attractant," Journal of Wildlife Management, 46(1):230-234 (1982).
Salzer, H. R. et al., "Growth and Nutritional Intake of Infants with Congenital Heart Disease," Pediatr. Cardiol., 10(1):17-23 (1989).
Stimson, D., "A Killer Yields to Modem Medicine," [online], MDA/Quest, vol. 10, No. 1 (Mar./Apr. 2003), http://www.mdausa.org/publications/Quest/q102pompe.cfm.
Sugden, M. C. et al., "Odd-carbon fatty acid metabolism in hepatocytes from starved rats," Biochemistry International., 8(1):61-67 (1984).
Valberg, S. J. et al., "Polysaccharide Storage Myopathy Associated with Recrrent Exertional Rhabdomyolysis in Horses," Neuromusc. Disord., 2(5/6):351-359 (1992).
Valberg, S. J. et al., "Tying-Up in Horses: The Syndrome, Known Causes, and New Treatments," Moorman's Feed Facts (Sep. 1995).
Valberg, S. J. et al., "Familial Basis of Exertional Rhabdomyolysis in Quarter Horse-related Breeds," Am. J. Vet. Res., 57(3):286-290 (1996).
Valberg, S. J. et al., "Skeletal Muscle Metabolic Response to Exercise in Horses with 'Tying-up' Due to Polysaccharide Storage Myopathy," Equine Vet. J., 31(1):43-47 (1999).
Valberg, S. J., et al., "Glycogen Branching Enzyme Deficiency in Quarter Horse Foals," J. Vet. Intern. Med., 15:572-580 (2001).
Valberg, S. J. "Tying-Up in Horses: Research Leads to Dietary and Exercise Management Strategies," Moorman's Feed Facts at http://www.moormans.com/equine/FFpdf/FFNov2k1.sub.--TyingUpInHorses.htm (2004).
Valentine, B. A. et al., "Clinical and Pathologic Findings in Two Draft Horses with Progressive Muscle Atrophy, Neuromuscular weakness, and Abnormal Gait Characteristic of Shivers Syndrome," JAVMA, 215(11):1661-1665 (1999).
Valentine, B. A. et al., "Polysaccharide Storage Myopathy in Morgan, Arabian, and Starndarbred Related Horses and Welsh-cross Ponies," Vet. Pathol., 37:193-196 (2000).
Valentine, B. A. et al., "Incidence of Polysaccharide Storage Myopathy in Draft Horse-related Breeds: A Necropsy Study of 37 Horses and a Mule," J. Vet. Diagn. Invest., 13:63-68 (2001).
Valentine, B. A., "Polysaccharide Storage Myopathy in Draft Horses: Only Recently Recognized and Already Controversial," at http://neahi.org/polysaccharide_storage_myopathy.htm (2004).
Vanitallie, T. B. et al., "Rats enriched with odd-carbon fatty acids: maintenance of liver glycogen during starvation," Science, 165(3895):811-813 (1969).
Van Kempen et al., "Medium-chain fatty acid oxidation in colostrum-deprived newborn piglets: stimulative effect of L- carnitine supplementation," J. Nutri., 123:1531-1537 (1993).
Vorgerd, M. et al., "Carbohydrate oxidation disorders of skelatal muscle," Curr. Opin. Cin. Nutr. Metab. Care., 5:611-617 (2002).
Williams, C. A. et al., "Plasma glucose and insulin responses of Thoroughbred mares fed a meal high in starch and sugar or fat and fiber," J. Anim. Sci., 79:2196-2201 (2001).
Winkel, L. P. F., et al., "Enzyme Replacement Therapy in Late-Onset Pompe's Disease: A Three-Year Follow-up," Ann. Neurol., 55:495-502 (2004).
"AESM Meeting Report" JEVS, 17(4):178-180 (1997).
Yang et al., "Identification of four novel mutations in patients with carnitine palmitoyltransferase II (CPT II) deficiency," Molecular Genetics and Metabolism, 64:229-236 (1998).

* cited by examiner

GLYCOGEN OR POLYSACCHARIDE STORAGE DISEASE TREATMENT METHOD

CROSS-REFERENCE TO RELATED APPLICATIONS

This application is a Continuation of U.S. patent application Ser. No. 13/343,578 filed Jan. 4, 2012 (now U.S. Pat. No. 8,697,748), which is a Divisional of U.S. patent application Ser. No. 11/172,693 filed Jul. 1, 2005 (now U.S. Pat. No. 8,106,093), which claims the benefit of U.S. Provisional Patent Application No. 60/585,502 filed Jul. 2, 2004. The present application claims priority to all of these applications which are hereby incorporated by reference in their entireties.

TECHNICAL FIELD OF INVENTION

This invention relates to the treatment of glycogen or polysaccharide storage diseases affecting humans and other animals, and more particularly, to formulations that ameliorate the symptoms of these diseases.

BACKGROUND OF THE INVENTION

Without limiting the scope of the invention, its background is described in connection with polysaccharide storage diseases.

Glycogen-storage disease type II ("GSD II" or "Pompe's disease"), is a genetic disorder in humans resulting from the deficiency of acid alpha-glucosidase ("acid maltase"), a lysosomal hydrolase enzyme. The disease is characterized by the abnormal accumulation of glycogen in the lysosomes. (Hirschhorn, R and Reuser, A J J: Glycogen Storage Disease Type II: Acid α-Glucosidase Deficiency. In: The Metabolic and Molecular Bases of Inherited Diseases, 8th edition, Chapter 135, pp 3389-3420, McGraw-Hill, 2001.). Polysaccharide storage diseases have also been reported in other animals, particularly in horses, cattle, and sheep.

With respect to humans, three major forms of GSD II have been described: infantile, juvenile, and adult-onset. See J. Ibrahim, et al., Glycogen Storage Disease Type II, http://www.emedicine.com/PED/topic1866.htm (2003). The infantile form of GSD II is described as presenting by 6 months of age and characterized by involvement of cardiac, skeletal and respiratory muscles with rapid progression to death by respiratory and cardiac failure. These inherited conditions are due to an enzyme-deficiency that occurs in the human population at about 1 in 14,000 to 1 in 60,000 live births. The infantile or neonatal form of the disease usually results in death by about twelve to eighteen months of age.

The juvenile (intermediate) form includes infants and children older than 6 months who present with weakness but generally have no cardiac disease. Adult-onset GSD II is slowly progressive and involves progressive muscle weakness that affects the accessory muscles of respiration and finally leads to respiratory failure and death. This form of the disease usually does not involve the heart. The adult-onset form of the disease may appear in the second or third decade of life, and as late as the sixth decade. The disease results in loss of weight and muscle mass. With the loss of muscle mass comes difficulty in breathing because the muscles have difficulty powering the breathing mechanism. The deficient enzyme, acid α-glucosidase, is not required for the vast majority of cellular glycogen because the main pathway for glycogen degradation is not deficient in GSD II disease, energy production is not impaired, and hypoglycemia does not occur. The main issue of deficiency of acid alpha-glucosidase enzymatic activity is the accumulation of structurally normal glycogen in lysosomes and cytoplasm in affected individuals. Excessive glycogen storage within lysosomes interrupts the normal functioning of other organelles and leads to cellular injury and dysfunction of the entire organ involved.

Presently, there is neither a cure for the disease, nor alteration of the clinical course of expected fatality, although some relief has been realized temporarily with high protein diets and with treatment for cardiac and respiratory failure. Alternatively, enzyme replacement therapy with recombinant human acid alpha-glucosidase, (rhGAA), an investigational enzyme replacement therapy for Pompe disease is now in clinical trials (www.genzyme.com and www.pompe.com).

Glycogen and other polysaccharide storage diseases also affect animals other than humans. For example, muscle disease in draft horses has been known for over 100 years, and in 1992 was correlated with polysaccharide storage diseases. Such disorders are commonly referred to as "Monday Morning Disease", "tying" or "locking up" or simply severe muscle disease have been reported. Draft horses which worked hard six days a week but were given a high grain diet and a day of rest on Sunday were found to be prone to massive muscle injury on Monday. Recently, the polysaccharide storage diseases have been found to be related to problems with giving a draft horse general anesthesia. In addition, glycogen branching enzyme deficiency has been reported as causing muscle weakness in Quarter Horses and related breeds. It is reportedly a separate disorder from polysaccharide storage myopathy and is a deficiency in the enzyme necessary for the formation of normal glycogen. S. Valberg, "Glycogen Storage Disorders of Quarter Horse Foals," J. Vet. Intern. Med. 15(6): 572-80 (2001).

A dietary solution has been suggested for the polysaccharide storage diseases using a diet with reduced starches and sugars and added fat as an alternative energy source. Providing fats as opposed to carbohydrates as an alternative source of energy to relieve tying up in horses has also been proposed. A subset of horses with chronic exertional rhabdomyolyis have an abnormal accumulation of glycogen (polysaccharide) stores in their muscles and one of the preventative measures suggested is feeding diets without grains and adding a fat supplement to maintain low blood glucose and insulin concentrations. L. Gray, "Polysaccharide Storage Myopathy (Glycogen Storage Disease)," Horse Previews, July 2002. These diets provide only partial relief, if at all, in these affected animals.

SUMMARY OF THE INVENTION

It has now been found that administering odd carbon fatty acids and/or ketones to humans and other animals can treat and ameliorate the effects of glycogen or polysaccharide storage diseases. More particularly, the present invention includes compositions, methods, feeds, diets, additives and the like for the treatment of polysaccharide storage diseases.

For example, the present invention includes a pharmaceutical composition for treating a glycogen storage disease that includes a pharmaceutically effective amount of an odd carbon fatty acid that is at least partially water-soluble for the treatment of the glycogen storage disease. The composition may also include a carrier, a diluent, e.g., a lipophilic diluent and/or an emulsifier. Non-limiting examples of useful emulsifiers include Imwitor 370, Imwitor 375, Imwitor 377, Imwitor 380 and Imwitor 829. In one embodiment, the odd carbon fatty acid is unneutralized and may be a C15, C7, C5 and mixtures or combinations thereof. For example, the odd carbon fatty acid may be 3-hydroxypentanoate, 3-ketopentanoate, tri-heptanoid, n-heptanoic acid and mixtures and combinations thereof. The compositions of the present invention may be provided to a patient suspected of having a Glycogen Storage Disease, such as Pompe's disease. The patient may be suspected of having an anapleurotic disease, that is, a disease with symptoms that may be ameliorated with anapleurotic precursors that serve have therapeutic effects.

For example, the composition of the present invention may be an odd carbon fatty acid that is adapted for a dosage of between 0.1, 1, 1.5, 2, 3 or even 4 gr/kg/day. One example of an odd carbon fatty acid for use with patients may have an acid value of 0.1 or less mg KOH/gr, a hydroxyl value of 2.8 or less mg KOH/gr. The odd carbon fatty acid may have a purity of at least about 98 percent, e.g., triheptanoate that is at least about 97% pure.

The present invention also includes a method of treating a patient suffering from Pompe's disease by administering to a patient in need thereof a composition that with a human recombinant α-glucosidase in a pharmaceutically acceptable carrier, in an amount insufficient to treat the disease and concurrently providing the patient with a pharmaceutically effective amount of an odd carbon fatty acid to reduce the amount of the recombinant α-glucosidase necessary to treat the patient. The amount of human recombinant α-glucosidase may be from about 0.01 to about 100 milligrams per 100 kilograms of patient per month. The α-glucosidase and pharmaceutically effective amount of an odd carbon fatty acid may be provided in a single-dose, e.g., intravenously. The odd carbon fatty acid may dosed at between 1 to 2 gr/kg/day and/or be 30 to 40 percent of total daily Kcalories. Generally, a patient's total caloric intake is between about 1,200 to 3,000 calories per day.

Another embodiment of the present invention is a method of treating a disease in a mammal resulting from deficiencies of fatty acid oxidaase disease by administering to the mammal a therapeutically effective amount of a pharmaceutical composition that includes a recombinant glycosylated enzymatically active α-glucosidase A or an enzymatically active fragment thereof and a pharmaceutically effective amount of an odd carbon fatty acid. By providing the patient with a supplemental source of anapleurotic carbon sources, the effective amount recombinant glycosylated enzymatically active α-glucosidase A or an enzymatically active fragment needed to treat a mammal is reduced by between about 20 and 80 percent. The mammal may be selected from humans, dogs, cats, horses, hamsters, rats, mice, sheep, goats and pigs. Depending on the course of treatment, specific disease, extent of the disease and other biochemical, metabolic and physiologic factors, the skilled artisan may be able to reduce the amount and total number of daily doses of pharmaceutical composition by half or less. The pharmaceutical composition may be administered orally, intravenously, intramuscularly, intranasally, intradermally, intraperitoneally, subcutaneously and/or as a suppository or by any other method known to those of skill in the pharmaceutical arts. The α-glucosidase A may further include a pharmacologically acceptable carrier, e.g., polyethylene glycol (PEG) and the amount of odd carbon fatty acid is sufficient to be detectable in serum as free heptanoate and/or metabolites thereof. By providing additional energetic support, the recombinant glycosylated enzymatically active α-glucosidase A or an enzymatically active fragment thereof is provided in a sub-optimal amount. The effective amount of the odd carbon fatty acid includes a nutritionally effective amount, that is, one that provides a measurable amount of change in a patient, e.g., decreased fatigue, increased energy, increased protein sparing and the like.

The present invention also includes a method of treating a glycogen storage disease by administering to a patient in need thereof a therapeutically effective amount of a pharmaceutical composition that includes an odd-chain fatty acid or ketone. The pharmaceutical composition is administered, e.g., at a daily oral administration dosage of between about 0.5 to about 2.0 grams, per day, per kilogram of patient weight. Useful dosage forms include those adapted for oral administration, e.g., powder, tablet, gelatin, gelcap, capsule, soft-gel, chewable or liquid form. For human patient's, therapeutically effective amount are between about 20 and 40% of the patient's daily caloric intake. The compositions may also be used for the treatment of muscle weakness by administering to a patient a therapeutically effective amount of a pharmaceutical composition with an odd-chain fatty acid or ketone, wherein the patient's muscle weakness is reduced and pulmonary function is increased. Muscle weakness may be the result of an underlying disease or may be caused by acute muscle usage, e.g., athletes, mountain climbers, spelunking, military operations, maneuvers, exercises and the like. The present invention will be particularly useful for chronic muscle weakness. The present invention may also be used in a treatment for urgency in urination and defecation by administering to a patient a therapeutically effective amount of a pharmaceutical composition with an effective amount of an odd-chain fatty acid or ketone that reduces the urgency to urinate and/or defecate.

Yet another method of the present invention includes a method for protein sparing in which a therapeutically effective amount of a pharmaceutical composition that includes an odd-chain fatty acid or ketone is administered to a patient in need of protein sparing. The composition may further includes one or more vitamins, minerals, amino acids, lipids, nucleic acids, co-factors, pro-vitamins, and combinations of mixtures thereof, e.g., a nutritionally effective amount of branched amino acids.

The present invention may be formulated into immediate release product with an at least partially water-soluble ketogenic odd-chain fatty acid in an immediate release form that becomes immediately bioavailable in a subject. Bioavailability in a subject may be determined by serum levels of odd-chain fatty acids, organic salts, acylcarnitines and carnitine levels from, e.g., dried blood spots (dbs), saliva, urine, tears, sweat, plasma, amniotic or cerebro-spinal fluid and the like. The product may be adapted for parenteral, intravenous, oral, intramuscular, intraaortal, intrahepatic, intragastric, intranasal, intrapulmonary, intraperitoneal, subcutaneous, rectal, vaginal, intraosseal or dermal delivery. The product may be provided together or separately with one or more vitamins, minerals, amino acids, lipids, nucleic acids, co-factors, pro-vitamins, and combinations of mixtures thereof. Examples of odd chain fatty acids may be produced by solution precipitation methods, anti-solvent precipitation, spray drying, spray freezing, evaporative precipitation into an aqueous solution, wet milling, mechanical milling, vacuum-drying, vacuum-heating or lyophilization. The odd chain fatty acids may be particles that are amorphous, crystalline or semi-crystalline. An example is produced by evaporative precipitation into an aqueous solution and the formulation has a drug-to-excipient ratio greater than about 3:1. The odd chain fatty acids may be a provided as a ketogenic odd-chain fatty acid-to-excipient ratio that is greater than about 1:10, 1:1, 5:1, 7:1 or 10:1. For example, the ketogenic odd-chain fatty acid-to-emulsifier ratio is about 1:10, 1:1, 4:1, 7:1, 10:1, 13:1, 15:1, 25:1 or 40:1, e.g., C7:Imwittor.

The present invention may also be used in a method of providing nutritional support for surgery by providing a patient in need of supplemental metabolic support a nutritionally effective amount of a ketogenic odd-chain fatty acid of between about 30-35% of total Kcal/day. The nutritional supplements may also be used in a method for ameliorating the effects of physical exertion, the method includes administration to a person in need of such amelioration a pharmaceutically or nutritionally effective amount of one or more of the odd chain fatty acids described herein. The odd chain fatty acids will also find particular uses as a post-operative nutritional support that includes a nutritionally effective amount of a compound that provides both 2-carbon and 3-carbon citric acid cycle metabolites. An example of a 2-carbon metabolite is acetyl-CoA and the 3-carbon metabolite is propionyl-CoA. The composition may also include a nutritionally effective amount of one or more essential fatty acids and/or one or more essential saccharides.

The odd chain fatty acids may even be provided in a modified release product having two portions, wherein a first portion includes a first quantity of a ketogenic odd-chain fatty acid in an immediate release form which becomes fully bioavailable in the subject's stomach and a second portion with a second compound in a sustained release form wherein the ratio of the first quantity to the second quantity provides a serum Cmax in a human subject equivalent to the serum Cmax obtained when the first of one or more doses of a standard immediate release formulation having one third the amount of the ketogenic odd-chain fatty acid is dosed every four hours over a 12 hour period and wherein the product also provides therapeutically effective bioavailability for at least twelve hours after a single dose in a human subject according to serum analysis. The second compound may even by the ketogenic odd-chain fatty acid and/or one or more vitamins, minerals, amino acids, lipids, nucleic acids, co-factors, provitamins, and combinations of mixtures thereof.

A diet is provided by the present invention that includes a ketogenic odd-chain fatty acid with between about 5 to 40% of total Kcal/day, essential fats of between about 5-20% total Kcal/day, carbohydrates restricted to about 20 to 40% total Kcal/day of the diet and a protein content of between about 15 to 30% total Kcal/day. The total Kcal/day of each of the fatty acid, fats, carbohydrates and/or protein can be varied depending on the particular need and application. For example, the essential fats provides between about 10-15% of the total Kcal/day, the daily carbohydrate intake provides about 30% of the total Kcal/day, the daily protein intake provides about 20% of the total Kcal/day or the ketogenic odd-chain fatty acid provides between about 1-4 gm/Kg/day. The skilled artisan will recognize the different variations and combinations available.

The ketogenic odd-chain fatty acid includes one or more odd-chain fatty acids selected from C5, C7, C 15, and mixtures or combinations thereof. In addition, the ketogenic odd-chain fatty acid includes triheptanoin, n-heptanoic acid, a triglyceride, or a salt or derivative thereof, or combinations thereof.

The present invention provides a beverage including water, carbohydrates, electrolytes and a ketogenic odd-chain fatty acid in a concentration of between about 0.5% to about 5.0%. The beverage includes ketogenic odd-chain fatty acid that have one or more odd-chain fatty acids selected from C5, C7, C15, and mixtures or combinations thereof. The ketogenic odd-chain fatty acid has a concentration of about 1.0% and in some instances, the fatty acid is emulsified. The beverage includes ketogenic odd-chain fatty acid that provides between about 20-30% of the daily caloric intake. The ingredients of the beverage include the following:

| Ingredient | Approximate Concentration |
| --- | --- |
| Potassium | 2 meq/l |
| Sodium | 26 meq/l |
| Glucose | 4% |
| Pyruvate | 1% |
| ketogenic odd-chain fatty acid | 1 to 20% |
| Emulsifier | 0.1 to 2.0% |
| water | balance. |

A beverage is also provided that provides a source of immediate energy that has a composition by weight:

| | |
| --- | --- |
| Total Carbohydrate | 0.4-3.5% |
| Ketogenic odd-chain fatty acid | 0.1 to 20% |
| Emulsifier | 0.1 to 2.0% |
| Sodium Chloride | 0.16-0.33% |
| Potassium Chloride | 0.03-0.13% |
| Free Citric Acid | 0.026-0.26% |
| Water | balance |

In addition to beverages, the present invention includes a dry beverage concentrate for enhanced, immediate energy requirements in a mammalian body that includes a composition by weight in water: an emulsified, ketogenic odd-chain fatty acid 0.1-25%, total carbohydrate of 0.4-3.5%, sodium chloride 0.16-0.22%, potassium chloride 0.03-0.13%, and free citric acid 0.026-0.26%, the concentrate suitable for mixture with water to yield a beverage. The skilled artisan will recognize that the weight of the component may be varied depending on the particular application.

A food is also provided that includes a mixture of ingredients selected to make one or more snacks, soups, salads, cakes, cookies, crackers, breads, ice creams, yogurts, puddings, custards, baby foods, medicinal foods, sports bars, breakfast cereals and beverages and a ketogenic odd-chain fatty acid in a concentration of between about 0.5% to about 5.0% of the composition. The food composition includes grains, fruits, nuts and supplemental dietary fiber in the form of compressed flakes, supplemental dietary fiber and combinations thereof. The present invention provides a food composition that includes compressed flakes of supplemental dietary fiber in the form of apple fiber, corn bran, soy fiber, pectin, guar gum, gum ghatti, and gum arabic, as well as mixtures thereof. Some embodiments of the present invention include one or more binder materials that include rice flour, wheat flour, oat flour, corn flour, rye flour and potato flour, as well as mixtures thereof.

The present invention also includes a pre-cooked edible and chewable product selected from the group consisting of breakfast cereals, snacks, soups, salads, cakes, cookies, crackers, puddings, ice creams, yogurts, puddings, custards, baby foods, medicinal foods, sports bars, and beverages. Additionally, the composition can be extrusion cooked. The present invention includes an ingredient for fortification of a food product that has an emulsified ketogenic odd-chain fatty acid in a concentration of between about 0.5% to about 5.0% of the food supplement.

An orally administratable partially dry unit dosage is provided that includes at least about 10 to 1,000 mg of a ketogenic odd-chain fatty acid. When in the form of a nutritional supplement includes a nutritionally effective amount of a ketogenic odd-chain fatty acid that are metabolized into both 2-carbon and 3-carbon citric acid cycle metabolites, and the ketogenic odd-chain fatty acid is selected from the group consisting of a C5, C7, C15, and mixtures or combinations thereof.

The present invention also includes a method for increasing the immediately available energy supply to a cell by exposing the cell to an effective dosage of a ketogenic odd-chain fatty acid that represents 20-35% of the cellular requirement of kCals per day.

A method for increasing the immediately available energy supply to a mammal by providing the mammal with an effective dosage of a ketogenic odd-chain fatty acid that comprises 30-35% of the mammal's kCal per day is also included. The ketogenic odd-chain fatty acid includes one or more odd-chain fatty acids selected from C5, C7, C15, and mixtures or combinations thereof.

The present invention also includes an animal feed that has an odd chain fatty acid present in an amount effective to provide nutritive fat to an animal and a solid nutritive source. The animal feed is adapted for use by one or more of poultry, livestock, farm-raised fish, crabs, shrimp and fresh-water turtles. The solid nutrititive source includes a source selected from the group consisting of soy, oats, sorghum, whole wheat, a nutritive wheat fraction, whole rice, a nutritive rice fraction, whole corn a nutritive corn fraction and whole barley, a nutritive barley fraction, vitamins and nutritive minerals. When used as an animal feed the odd chain fatty acid is present in an amount of at least about 5% to 40% by weight of the feed.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
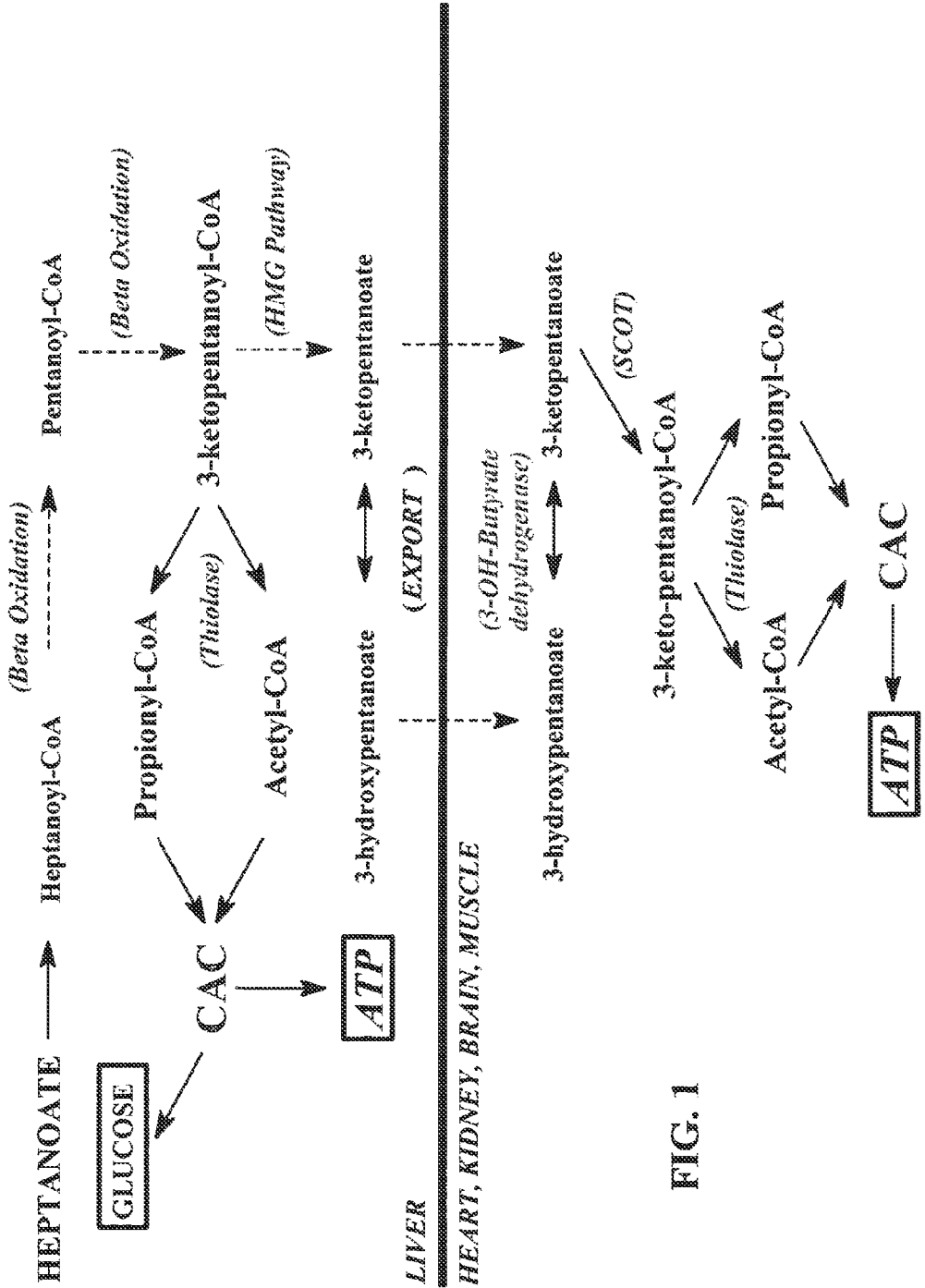
FIG. 1 is a schematic drawing depicting the metabolic fate of the odd-carbon fatty acid, heptanoate (C7), derived from the triglyceride, Triheptanoin.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. As such, unless otherwise indicated, the terms "a" and "an" are taken to mean "one", "at least one" or "one or more". The terminology herein is used to describe specific embodiments of the invention, but their usage does not delimit the invention, except as outlined in the claims.

As used herein, the terms "subject" or "patient" are intended to include living organisms that may have one or more conditions generally referred to as polysaccharide storage diseases. Examples of subjects include humans, monkeys, horses, cows, sheep, goats, dogs, cats, mice, rats, and transgenic species thereof. Other examples of subjects include experimental animals such as mice, rats, dogs, cats, goats, sheep, pigs, and cows. A subject can be a human suffering from, or suspected of having, a polysaccharide storage disease, e.g., a glycogen storage disease such as Pompe's disease (GSD II).

As used herein, the phrases "therapeutically effective dosage" or "therapeutically effective amount" is an amount of a compound or mixtures of compounds, such as the odd-chain fatty acids and precursors or derivatives thereof, that reduce the amount of one or more symptoms of the condition in the infected subject by at least about 20%, at least about 40%, even more at least about 60%, 80% or even 100% relative to untreated subjects. Active compounds are administered at a therapeutically effective dosage sufficient to treat a condition associated with a condition in a subject. For example, the efficacy of a compound can be evaluated in patients or animal model systems that may be predictive of efficacy in treating the disease in humans or animals.

As used herein the term, "essential fatty acids" is used to describe fats and oils in foods are made up of basic units called fatty acids. In the body, these typically travel in three's as fatty acid chains attached to glycerol, forming a triglyceride. Based on their chemical structure, fatty acids are classified into 3 major categories: monounsaturated, polyunsaturated, or saturated fats. The oils and fats that people and animals eat are nearly always mixtures of these 3 types of fatty acids, with one type predominating. Two specific types of polyunsaturated fatty acids, linoleic and alpha-linolenic, are called essential fatty acids. They must be present in the diet in adequate amounts because they are considered necessary for proper nutrition and health. Linoleic acid (LA) is an omega-6 fatty acid and is found in many oils, e.g., corn, safflower, soybean and sunflower, whole grains and walnuts. Alpha-linolenic acid (ALA) is a plant precursor of docosahexanoic acid (DHA). Sources of ALA include seaweeds and green leaves of plants (in very small amounts), soybeans, walnuts, butternuts, some seeds (flax, chia, hemp, canola) and the oils extracted from these foods.

As used herein, the term "nutritionally effective amount" is used to mean the amount of odd chain fatty acids that will provide a beneficial nutritional effect or response in a mammal. For example, as with a nutritional response to vitamin- and mineral-containing dietary supplements varies from mammal to mammal, it should be understood that nutritionally effective amounts of the odd chain fatty acids will vary. Thus, while one mammal may require a particular profile of vitamins and minerals present in defined amounts, another mammal may require the same particular profile of vitamins and minerals present in different defined amounts. Such is the case with the nutritionally effective amounts of the odd chain fatty acids of the present invention, in which the supplementation may be used to add C3 and C2 carbon chains into the liver and/or the heart, muscle, brain and kidney.

When provided as a dietary supplement or additive, the odd chain fatty acids of the invention has been prepared and administered to mammals in powdered, reconstitutable powder, liquid-solid suspension, liquid, capsule, tablet, caplet, lotion and cream dosage forms. The skilled artisan in the science of formulations can use the odd chain fatty acids disclosed herein as a dietary supplement that may be formulated appropriately for, e.g., irrigation, ophthalmic, otic, rectal, sublingual, transdermal, buccal, vaginal, or dermal administration. Thus, other dosage forms such as chewable candy bar, concentrate, drops, elixir, emulsion, film, gel, granule, chewing gum, jelly, oil, paste, pastille, pellet, shampoo, rinse, soap, sponge, suppository, swab, syrup, chewable gelatin form, chewable tablet and the like, can be used.

Due to varying diets among people, the dietary odd chain fatty acids of the invention may be administered in a wide range of dosages and formulated in a wide range of dosage unit strengths. It should be noted that the dosage of the dietary supplement can also vary according to a particular ailment or disorder that a mammal is suffering from when taking the supplement. For example, a person suffering from chronic fatigue syndrome or fibromyalgia will generally require a dose different than an athlete that is wanting to attain a nutritional benefit. An appropriate dose of the dietary supplement can be readily determined by monitoring patient response, i.e., general health, to particular doses of the supplement. The appropriate doses of the supplement and each of the agents can be readily determined in a like fashion by monitoring patient response, i.e., general health to particular doses of each.

The odd chain fatty acids may be administered simultaneously or sequentially in one or a combination of dosage forms. While it is possible and even likely that the present dietary supplement will provide an immediate overall health benefit, such benefit may take days, weeks or months to materialize. Nonetheless, the present dietary odd chain fatty acid supplement will provide a beneficial nutritional response in a mammal consuming it.

The odd-chain fatty acids of the present invention may be administered, e.g., orally or by subcutaneous, intravenous, intraperitoneal, etc., administration (e.g. by injection). Depending on the route of administration, the active compound may be neutralized, made miscible, at least partially or fully water-soluble or even coated in a material to protect the odd-chain fatty acids from the action of bases, acids, enzymes or other natural conditions that may interfere with their effectiveness, uptake or metabolic use.

To administer the therapeutic compound by other than parenteral administration, it may be necessary to coat the compound with, or co-administer the compound with, a material to prevent its inactivation. For example, the therapeutic compound may be administered to a subject in an appropriate carrier, for example, emulsifiers, liposomes, or a diluent. Pharmaceutically acceptable diluents include saline and aqueous buffer solutions. The therapeutic odd-chain fatty acids may be dispersed in glycerol, liquid polyethylene glycols, and mixtures thereof and in oils. Under ordinary conditions of storage and use, these preparations may contain a preservative to prevent the growth of microorganisms.

Pharmaceutical compositions that include the odd-chain fatty acids of the present invention suitable for injectable use may include sterile aqueous solutions, dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi.

The odd-chain fatty acids may be provided with a carrier in a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The odd-chain fatty acids may be provided in one or more controlled sizes and characteristics with one or more water-soluble polymers depending on the size and structural requirements of the patient, e.g., the particles may be small enough to traverse blood vessels when provided intravenously. Either synthetic or naturally occurring polymers may be used, and while not limited to this group, some types of polymers that might be used are polysaccharides (e.g. dextran, ficoll), proteins (e.g. poly-lysine), poly(ethylene glycol), or poly(methacrylates). Different polymers, because of their different size and shape, will produce different diffusion characteristics for the odd-chain fatty acids in the target tissue or organ.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, methods of preparation include: vacuum drying, spray freezing, freeze-drying and the like, which yield a powder of the active ingredient (i.e., the therapeutic compound) plus any additional desired ingredient from a previously sterile-filtered solution thereof.

The odd-chain fatty acids can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. The odd-chain fatty acids may be incorporated with excipients and used in the form of ingestible tablets, buccal tablets, troches, capsules, elixirs, suspensions, syrups, wafers, and the like. The amount of odd-chain fatty acids in the compositions and preparations may, of course, be varied depending on, e.g., the age, weight, gender, condition, disease and course of treatment of the individual patient. Pediatric doses are likely to differ from adult doses as will be known to the skilled artisan. The amount of the therapeutic compound in such therapeutically useful compositions is such that a suitable dosage will be obtained.

A dosage unit for use with the odd chain fatty acids disclosed herein may be a single compound or mixtures thereof with other compounds, e.g., amino acids, nucleic acids, vitamins, minerals, pro-vitamins and the like. The compounds may be mixed together, form ionic or even covalent bonds. For pharmaceutical purposes the odd chain fatty acids (e.g., C5, C7 and C15) of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the odd chain fatty acids of the present invention to a patient in need of therapy that includes a number of conditions, e.g., polysaccharide storage diseases, fatigue, low energy, wasting and the like. The odd chain fatty acids may also be administered as any one of known salt forms.

The total daily amount of odd chain fatty acids will vary depending on the condition and needs of a patient. For example, the odd chain fatty acids may be provided as a supplemental source of immediate, short-term, mid-term or long-term energy and may be provided in formulations that are immediately available, slow release or extended release. The dosage amount may be measured in grams per day, as a percentage of kCalories consumed in a day, as a percentage of the total daily caloric intake, as part of a fixed, a modified or a diet that changes over time. For example, a patient may need immediate intervention that "spikes" the amount of odd chain fatty acids to approach or reach ketosis. These "ketogenic" odd chain fatty acids will then be varied to not have other side effects, e.g., start with 40% of total caloric intake per day and then reduced over time as the patient's condition, symptoms, clinical course and/or metabolic conditions improves. The range of percentage caloric intake may vary from between about 0.01, 0.1, 1, 2, 5, 10, 15, 20, 22, 25, 30, 35, 40 or even higher percent, which may include one or more of the odd chain fatty acids (e.g., C5, C7 or C15 (available from, e.g., Sassol, Germany). One way to measure the effect and/or dosing of the odd chain fatty acids is to measure the amount that is detectable in body solids or fluids, e.g., biopsies and blood, respectively. A wide variety of odd chain fatty acids metabolites may be detected from multiple sources, e.g., urine, tears, feces, blood, sweat, breath and the like.

For example, when using C7 as the source of odd chain fatty acids these can be provided in the form of a triglyceride, e.g., tri-heptanoin. The triglyceride triheptanoin is provided in a concentration sufficient to provide a beneficial effect is most useful in this aspect of the present invention. The seven-carbon fatty acid may be provided, e.g.:

| Infants | 1-4 g/kg | 35% kcalories |
| Children | 3-4 g/kg | 33-37% kcalories |
| Adolescent | 1-2 g/kg | 35% kcalories |
| Adults | 0.1-2 g/kg | 35% kcalories |

Goals have been set using 4 g/kg (within ideal body weight (IBW) range) for infants, children, and some adolescents. Goals have been set using 2 g/kg (within IBW range) for adolescents. Goals have been set using 2 g/kg (within IBW range) for adults; but toleration is 1-1.2 g per kg (which is 35% kcal of estimated needs).

The odd chain fatty acids are typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the odd chain fatty acids may be formulated to provide, e.g., maximum and/or consistent dosing for the particular form for oral, rectal, topical, intravenous injection or parenteral administration. While the odd chain fatty acids may be administered alone or pure, they may also be provided as stable salt form mixed with a pharmaceutically acceptable carrier. The carrier may be solid or liquid, depending on the type and/or location of administration selected.

Techniques and compositions for making useful dosage forms using the present invention are described in one or more of the following references: Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.), and the like, relevant portions of each incorporated herein by reference.

Odd chain fatty acids may be administered in the form of an emulsion and/or liposome, e.g., small unilamellar vesicles, large unilamellar vesicles and multilamellar vesicles, whether charged or uncharged. Liposomes may include one or more: phospholipids (e.g., cholesterol), stearylamine and/or phosphatidylcholines, mixtures thereof, and the like. Examples of emulsifiers for use with the present invention include: Imwitor 370, Imwitor 375, Imwitor 377, Imwitor 380 and Imwitor 829.

The odd chain fatty acid vesicles may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylaspartamidephenol, or polyethyleneoxide-polylysine substituted with palmitoyl residues, mixtures thereof, and the like. Furthermore, the vesicles may be coupled one or more biodegradable polymers to achieve controlled release of the odd chain fatty acids. Biodegradable polymers for use with the present invention include, e.g., polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

In one embodiment, gelatin capsules (gelcaps) may include the odd chain fatty acid in its native state. For oral administration in a liquid dosage form, the oral drug components may be combined with any oral, non-toxic, pharmaceutically acceptable inert carrier such as an emulsifier, a diluent or solvent (e.g., ethanol), glycerol, water, and the like. Examples of suitable liquid dosage forms include oily solutions or suspensions in water, pharmaceutically acceptable fats and oils, alcohols or other organic solvents, including esters, emulsions, syrups or elixirs, suspensions, solutions and/or suspensions reconstituted from non-effervescent granules and even effervescent preparations reconstituted from effervescent granules. Such liquid dosage forms may contain, for example, suitable solvents, preservatives, emulsifying agents, suspending agents, diluents, sweeteners, thickeners, and melting agents, mixtures thereof, and the like.

Liquid dosage forms for oral administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Solutions for parenteral administration include generally, a water soluble salt of the active ingredient, suitable stabilizing agents, and if necessary, buffering salts. Antioxidizing agents such as sodium bisulfite, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propyl-paraben, and/or chlorobutanol. Suitable pharmaceutical carriers are described in multiple editions of Remington's Pharmaceutical Sciences, Mack Publishing Company, a standard reference text in this field, relevant portions incorporated herein by reference.

For direct delivery to the nasal passages, sinuses, mouth, throat, esophagus, trachea, lungs and alveoli, the odd chain fatty acids may also be delivered as an intranasal form via use of a suitable intranasal vehicle. For dermal and transdermal delivery, the odd chain fatty acids may be delivered using lotions, creams, oils, elixirs, serums, transdermal skin patches and the like, as are well known to those of ordinary skill in that art. Parenteral and intravenous forms may also include pharmaceutically acceptable salts and/or minerals and other materials to make them compatible with the type of injection or delivery system chosen, e.g., a buffered, isotonic solution.

To the extent that the odd chain fatty acids may be made into a dry powder or form, they may be included in a tablet. Tablets will generally include, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with a non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methyl cellulose, agar, bentonite, xanthan gum, mixtures thereof, and the like.

Capsules. Capsules may be prepared by filling standard two-piece hard gelatin capsules each with 10 to 500 milligrams of powdered active ingredient, 5 to 150 milligrams of lactose, 5 to 50 milligrams of cellulose and 6 milligrams magnesium stearate.

Soft Gelatin Capsules. The odd chain fatty acids may be dissolved in an oil, e.g., a digestible oil such as soybean oil, cottonseed oil or olive oil. Non-digestible oils may also be used to have better control over the total caloric intake provided by the oil. The active ingredient is prepared and injected by using a positive displacement pump into gelatin to form soft gelatin capsules containing, e.g., 100-500 milligrams of the active ingredient. The capsules are washed and dried.

Tablets. A large number of tablets are prepared by conventional procedures so that the dosage unit was 100-500 milligrams of active ingredient, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption.

To provide an effervescent tablet, appropriate amounts of, e.g., monosodium citrate and sodium bicarbonate, are blended together and then roller compacted, in the absence of water, to form flakes that are then crushed to give granulates. The granulates are then combined with the active ingredient, drug and/or salt thereof, conventional beading or filling agents and, optionally, sweeteners, flavors and lubricants.

Injectable solution. A parenteral composition suitable for administration by injection is prepared by stirring sufficient active ingredient in deionized water and mixed with, e.g., up to 10% by volume propylene glycol, salts and/or water to deliver a composition, whether in concentrated or ready-to-use form. Given the nature of the odd chain fatty acids (alone, partially or fully-soluble in water) the amount and final concentration of the odd chain fatty acids may be varied such that the liquid may be provided intravenously using syringes and/or standard intravenous liquids or fluids. The solution will generally be made isotonic with sodium chloride and sterilized using, e.g., ultrafiltration.

Suspension. An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

Mini-tablets. For mini-tablets, the active ingredient is compressed into a hardness in the range 6 to 12 Kp. The hardness of the final tablets is influenced by the linear roller compaction strength used in preparing the granulates, which are influenced by the particle size of, e.g., the monosodium hydrogen carbonate and sodium hydrogen carbonate. For smaller particle sizes, a linear roller compaction strength of about 15 to 20 KN/cm may be used.

Kits. The present invention also includes pharmaceutical kits useful, for example, for providing an immediate source of alternative cellular energy, e.g., before, during or after surgery. The dosage will generally be prepared sterile and ready-to-use, e.g., one or more containers that may be broken (e.g., sealed glass ampoules), pierced with a syringe for immediate administration or even a pressurized container. Such kits may further include, if desired, one or more of various conventional pharmaceutical kit components, such as, for example, containers with one or more pharmaceutically acceptable diluents, carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit. It should be understood that although the specified materials and conditions are important in practicing the invention, unspecified materials and conditions are not excluded so long as they do not prevent the benefits of the invention from being realized.

Pharmaceutical Dosage Forms. The odd chain fatty acids of the present invention may be provided in liquid form or may also be provided in a capsule, gelcap or other encapsulated form. Generally, one composition of the present invention is prepared by adding, e.g., half of the Kaolin clay or other carrier into the blended followed by addition of a first active salt form, e.g., the salt form that is less soluble in the final liquid suspension, e.g., as an emulsion in water. This process is particularly suitable for very large mixtures, e.g., 500, 1,000, 3,000 or even 5,000 liters.

One particular method of delivery of the odd chain fatty acids of the present invention is in a tablet, capsule or gelcap that is coated for enteric delivery. Enteric coating relates to a mixture of pharmaceutically acceptable excipients that is applied to, combined with, mixed with or otherwise added to a carrier to deliver the medicinal content, in this case one or more odd chain fatty acids (e.g., C5, C7, C15, mixtures and combinations thereof) through the stomach unaltered for delivery into the intestines. The coating may be applied to a compressed or molded or extruded tablet, a gelatin capsule, and/or pellets, beads, granules or particles of the carrier or composition. The coating may be applied through an aqueous dispersion or after dissolving in appropriate solvent. Additional additives and their levels, and selection of a primary coating material or materials will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; easy application as a coating (substrate friendly); and economical practicality. Methods for enteric coating are well known in the art.

Remington's Pharmaceutical Sciences, discloses that enteric polymer carries generally include carboxyl groups and hydrophobic groups in the molecule and the enteric polymer is dissolved in a solvent having a specific pH value through the dissociation of the carboxyl groups. For instance, commercially available hydroxypropylmethyl cellulose acetate succinate is a derivative of hydroxypropylmethyl cellulose which is substituted with carboxyl groups (succinoyl groups) and hydrophobic groups (acetyl groups). Alginic acid, sodium alginate other natural materials may also be used to provide an enteric coating.

Other additives and excipients may then be added to the formulation of the partially water soluble carrier-active odd chain fatty acids mixture, e.g., adding Povidone (e.g., Povidone 30), Xantham gum (or other gums) and Sorbitol to a mixture of Kaolin Clay to provide a specific example of one formulation of the present invention. As will be apparent to those of skill in the art, the actual amount of the partially-excipient soluble active salt (e.g., non or partially water soluble) may be varied in accordance with the dissolution characteristics of the active, which may be further varied by addition of agents that affect the solubility and/or dissolution of the active in, e.g., water. As regards a pediatric formulation, the amount of active may be reduced in accordance with the dosage form approved for pediatric use.

One example of a liquid odd chain fatty acid(s) pharmaceutical composition may be prepared with the following components:

| Components | Weight |
| --- | --- |
| Odd chain fatty acid(s) | 1.0 Kg |
| emulsifier (e.g., Imwitor 375) | 100 gr |
| Purified water (USP) | 2.0 Kg |

The formulation may further include, e.g.:

| | |
| --- | --- |
| Glycerin (USP) | 500.0 ml |
| Sorbitol Solution, 70% (USP) | 500.0 ml |
| Saccharin Sodium (USP) | 10.0 gr |
| Citric Acid (USP) | 10.0 gr |
| Sodium Benzoate (NF) | 6.0 gr |
| Kollidon 30 | 330.0 gr |
| Xanthan Gum 200 Mesh | 20.0 gr |
| Bubble Gum Flavor | 11.1 gr |
| Methylparaben | 1.0 gr |
| Proplyparaben | 100 mg |
| Propylene Glycol (USP) | 75 ml |
| Additional ddH$_2$O | QS to 5 liters. |

With appropriate increases of the above for scale-up.

A batch of mixed release odd chain fatty acids in an enveloped preparation on a carrier, e.g., beads, may be prepared with the following components:

| Components | Weight |
| --- | --- |
| Emulsified odd chain fatty acids | 8.0 mg |
| Carrier | 51.7 mg |
| Calcium Stearate | 4.0 mg |
| Talc | 4.0 mg |
| Pharmaceutical Glaze | 5.5 mg |

When combining odd chain fatty acids (C5, C7 and/or C15), these may be formulated as follows. A capsule for extended release of a first active and extended release of a second active in an enveloped formulation, in a single capsule:

| First Bead | Weight | Second Bead | Weight |
| --- | --- | --- | --- |
| odd chain fatty acid C7 | 6.0 mg | odd chain fatty acid C15 | 2.0 mg |
| Bead | 162.9 mg | Bead | 108.5 mg |
| Lacquer | 6 mg | Lacquer | 3.3 mg |
| Talc | 12.6 mg | Talc | 5 mg |
| Calcium Stearate | 12.6 mg | Calcium Stearate | 5 mg |
| Capsule | 1 | | |

When combining the odd chain fatty acids, these may be formulated as follows. A capsule for extended release of a first active and extended release of a second active in an enveloped formulation, in a single capsule:

| First Bead | Weight | Second Bead | Weight |
| --- | --- | --- | --- |
| odd chain fatty acid C5 | 6.0 mg | odd chain fatty acids C7 | 2.0 mg |
| Bead | 162.9 mg | Bead | 108.5 mg |
| Lacquer | 6 mg | Lacquer | 3.3 mg |
| Talc | 12.6 mg | Talc | 5 mg |
| Calcium Stearate | 12.6 mg | Calcium Stearate | 5 mg |
| Mini-capsule | 1 | | |

A formulation for extended release of odd chain fatty acids of a second active in an enveloped formulation, in a gelcap:

| Component | Weight | Component | Weight |
| --- | --- | --- | --- |
| odd chain fatty acid | 6.0 mg | odd chain fatty acid | 2.0 mg |
| Bead | 162.9 mg | Bead | 108.5 mg |
| Lacquer | 6 mg | Lacquer | 3.3 mg |
| Talc | 12.6 mg | Talc | 5 mg |
| Calcium Stearate | 12.6 mg | Calcium Stearate | 5 mg |
| Gelcap | 1 | | |

A formulation for rectal release of odd chain fatty acids in a suppository:

| Component | Weight |
| --- | --- |
| Odd chain fatty acids | 100 mg |
| Carrier | 10 mg |
| Talc | 12.6 mg |
| Calcium Stearate | 12.6 mg |
| beeswax/glycerol | 1-2 gr |

An enteric-coated soft gelatin capsule that includes the odd chain fatty acids (with or without an emulsifier) is made by coating the odd chain fatty acids with a lipophilic material to obtain granules, mixing the granules obtained in step with an oily matrix, antioxidants and preservatives to form a lipid suspension, mixing the lipid suspension within a soft gelatin film, and coating the soft gelatin film to obtain an enteric coated soft gelatin capsule.

The odd chain fatty acid(s), stearic acid and triethanolamine are heated and mixed to form an emulsified fluid. The resulting emulsified fluid is mixed well by a homogenizer to obtain an emulsified suspension and enterically coated. Examples of formulations include:

| Component | Weight |
| --- | --- |
| Odd Chain Fatty Acids | 360.0 g |
| Stearic acid | 78.6 g |
| Ethanolamine | 21.4 g |
| Odd Chain Fatty Acids | 360.0 g |
| Stearic acid | 30.0 g |
| Triethanolamine | 20.0 g |
| Odd Chain Fatty Acids | 400.0 g |
| Stearic acid | 77.0 g |
| Ethanolamine | 23.0 g |
| Cetyl alcohol | 50.0 g |
| Odd Chain Fatty Acids | 245.0 g |
| Stearic acid | 38.5 g |
| Ethanolamine | 11.5 g |
| Cetyl alcohol | 50.0 g |
| Carboxymethyl cellulose | 25.0 g |

TABLE 1

Recommended Daily Nutrient Intake Ranges
RECOMMENDED DAILY NUTRIENT INTAKE
RANGES WITH FOD DEFECT

| AGE | NUTRIENT | | | |
| --- | --- | --- | --- | --- |
| | Protein | Energy | Fluid | C7 |
| | % of energy | kcal/kg/day | mL/kg | % Kcal/d |
| INFANTS | | | | |
| 0-<3 mo | 10-12% | 120 | 150-125 | 35% |
| 3-6 mo | 10-12% | 115 | 160-130 | 35% |
| 6-9 mo | 10-12% | 110 | 145-125 | 35% |
| 9-12 mo | 10-12% | 105 | 135-120 | 35% |

TABLE 1-continued

Recommended Daily Nutrient Intake Ranges
RECOMMENDED DAILY NUTRIENT INTAKE
RANGES WITH FOD DEFECT

| AGE | NUTRIENT | | | |
| --- | --- | --- | --- | --- |
| | Protein | Energy | Fluid | C7 |
| | g/kg | kcal/kg/day | mL/day | % Kal/d |
| Children | | | | |
| 1-3 years | 2-2.8 | 102 | 900-1800 | 35% |
| 4-6 years | 2 | 90 | 1300-2300 | 35% |
| 7-10 years | 1.5 | 70 | 1650-3300 | 35% |
| WOMEN | | | | |
| 11-14 years | 1 | 47 | 1500-3000 | 35% |
| 15-18 years | 0.8 | 40 | 2100-3000 | 35% |
| >18 years | 0.8 | 20-25 | 1400-2500 | 35% |
| MEN | | | | |
| 11-14 years | 1 | 55 | 2000-3700 | 35% |
| 15-18 years | 0.9 | 45 | 2100-3900 | 35% |
| >18 years | 0.8 | 20-25 | 2000-3300 | 35% |

If patient is >20% ideal body weight (IBW), use upper range IBW to calculate needs It has now been found that administration of odd carbon fatty acids that are converted or metabolized to the 5 carbon ketone bodies 3-hydroxypentanoate (BHP) and 3-ketopentanoate (BKP) is an effective treatment for GSDII in humans and polysaccharide storage diseases in horses and other animals. In addition, administration of the 5 carbon ketone bodies BHP and/or BKP in the form of either free ketone bodies or in other forms capable of providing the free ketones in vivo after administration is also an effective treatment for these diseases. Such forms of BHP and/or BKP as a triglyceride form, a polymeric form or a salt form could be used. The method of the invention spares the patient's own muscle protein because the patient no longer requires amino acids from the muscle for an energy source. In addition, the patient no longer requires the glycogen stored in the lysosomes as an energy source. The glycogen stored in the lysosomes will gradually decrease, because there is an intact glycogen degradative pathway in the cytosol that can compensate for the defective lysosomal pathway due to the absence of acid maltase (alpha glucosidase) in GSD II. Lysosomal "acid maltase" also has debrancher enzyme activity as well as alpha glucosidase activity. In the cytosolic glycogenoses, glycogen can enter the lysosome and degradation can be carried out by acid maltase since it has both glucosidase and debrancher activities.

The effective therapeutic agent in vivo is a product of the metabolism of C15, C7 or C5, or any other odd-carbon fatty acid that breaks down metabolically to BHP and BKP in the subject animal. FIG. 1 depicts the metabolic fate of C7 in humans. In addition, the C5 ketone bodies BHP and BKP, as stated above, could also be used directly for therapy. The degradation of C15, C7, & C5 all lead to the production of BHP and BKP and their export to other organ systems from the liver, as shown in FIG. 1.

Figure 2:
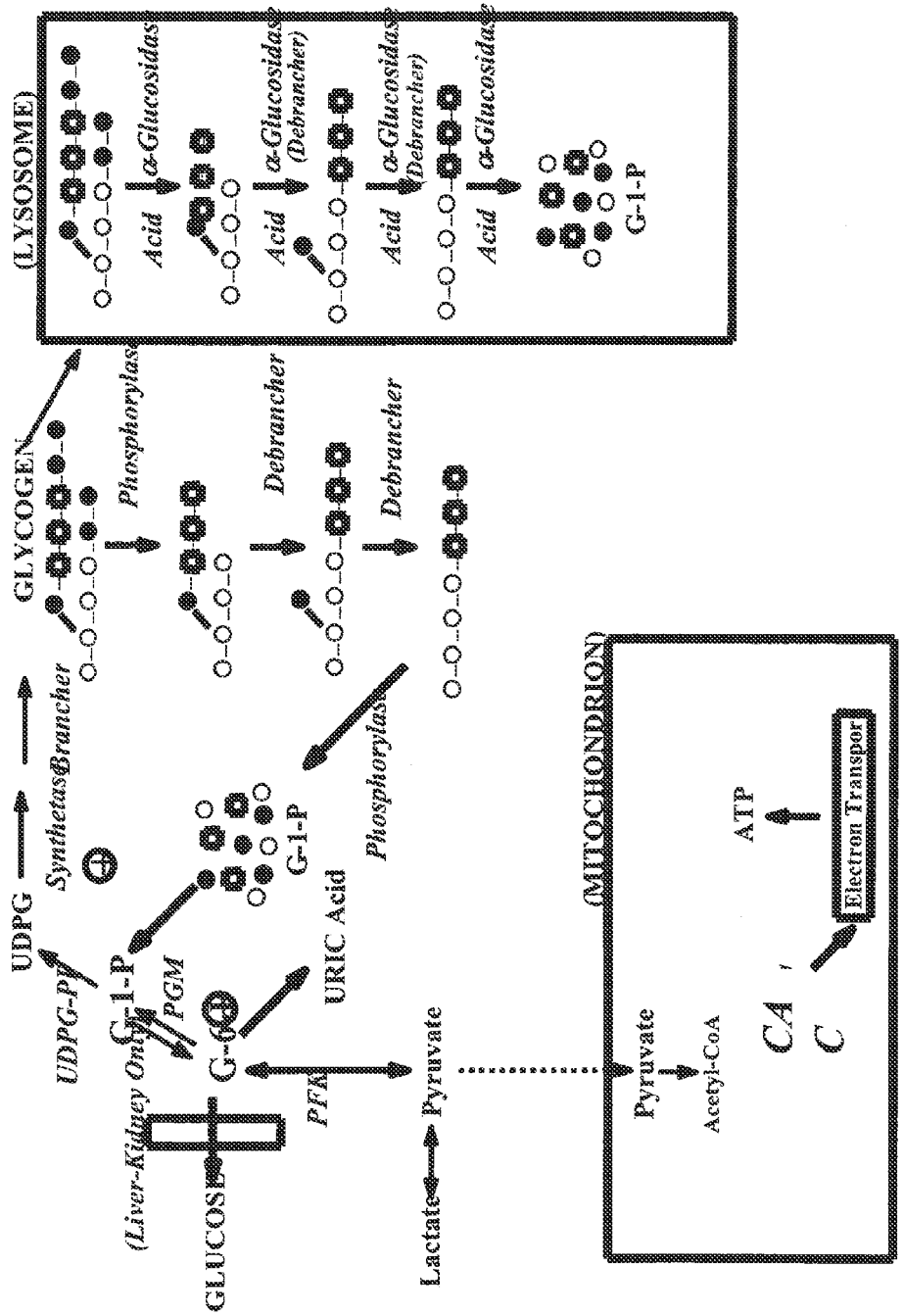
FIG. 2 is a schematic drawing depicting the organellar integration of glycogen metabolism in cells.
Figure 5:
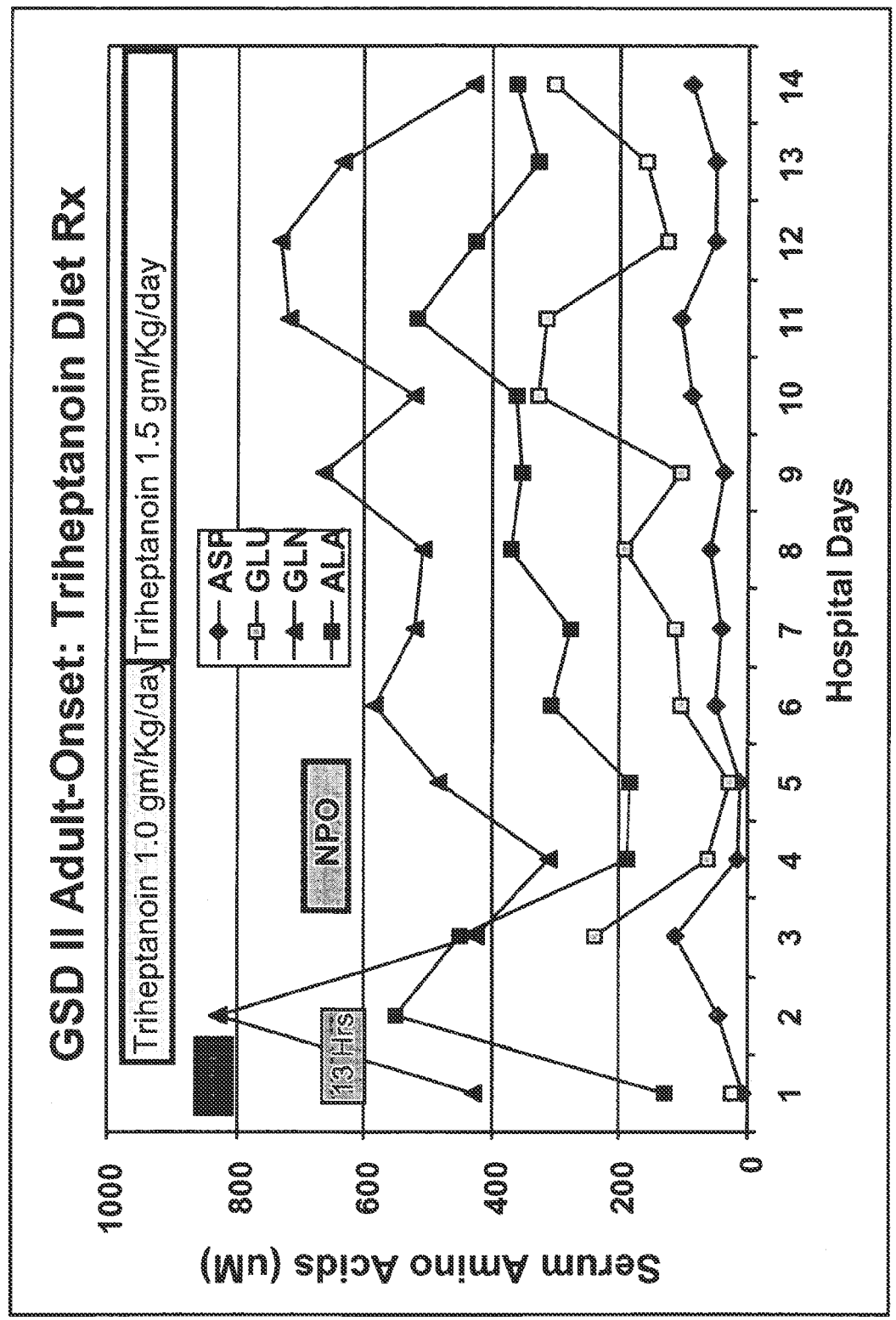
FIG. 5 depicts the effect of a triheptanoin-containing diet on the levels of selected amino acids in the blood of a patient with the adult onset form of glycogen storage disease II (acid maltase deficiency) with a diet containing Triheptanoin at a dose of 1.0 to 1.5 gm/kg/day)

Referring now to FIG. 2, the glycogen molecule is a polymer produced from the union of glucose molecules in a straight chain of glucose molecules joined together in α 1,4 linkage as well as branching of glucose residues in an α 1,6 linkage between glucose residues. This structure is represented schematically by a chain having a branch in this figure involving glucose residues depicted in red, blue and green. The branch (α1,6 linkage) is depicted in (red). In the cytosol, a phosphorylase enzyme is required to remove the blue residues. A debrancher enzyme is required to remove and relocate the green glucose residues to the end of the α 1,4 chain. The debrancher enzyme also clips the 1 to 6 branched residue as glucose-1-phosphate and the final product is a straight chain of glucose residues (blue) in α 1,4 linkage. This chain is completely degraded to glucose-1-phosphate residues. Table 2 shows the profound effect of C7 therapy on amino acid levels in the blood. After 13 and 41 hours the levels of Alanine, for example, had greatly increased. The patient was then off the C7 diet during a gastrostomy and the level decreased. Once the C7 diet was re-initiated, the Alanine levels rapidly increased. FIG. 5 shows the metabolism of C7 in the cytosol and the lumen of the mitochondria and demonstrates the locations and entry of the ketogenic odd chain fatty acids of the present invention.

TABLE 2

Plasma Amino Acids (uM/L) During Initiation of Anaplerotic Therapy, Adult-Onset Glycogen Storage Disease II (Pompe's).

| | Event: | Admit | C7 = 1.0 gm/Kg | | NPO* | | C7 = 1.5 gm/Kg | |
|---|---|---|---|---|---|---|---|---|
| | Time: | Baseline | 13 hrs | 41 hrs | 65 hrs | 84 hrs | 108 hrs | 132 hrs |
| ALANINE | (162-572) | 129 | 551 | 450 | 189 | 184 | 307 | 277 |
| GLUTAMINE | (424-720) | 430 | 827 | 424 | 313 | 483 | 584 | 519 |
| LEUCINE | (60-204) | 104 | 154 | 266 | 158 | 108 | 238 | 220 |
| VALINE | (108-295) | 188 | 333 | 384 | 200 | 183 | 304 | 269 |
| ISOLEUCINE | (39-119) | 58 | 81 | 138 | 87 | 61 | 144 | 128 |

*NPO for gastrostomy—IV glucose only;
**Essential amino acids

In the lysosome, another pathway exists for glycogen degradation. The lysosomal α-glucosidase enzyme (acid maltase) is not only a glucosidase, but also has the capability to act as a debrancher enzyme as well. These characteristics of the lysosomal α-glucosidase permit complete degradation of lysosomal glycogen. These features are illustrated schematically in FIG. 2.

Figure 3:
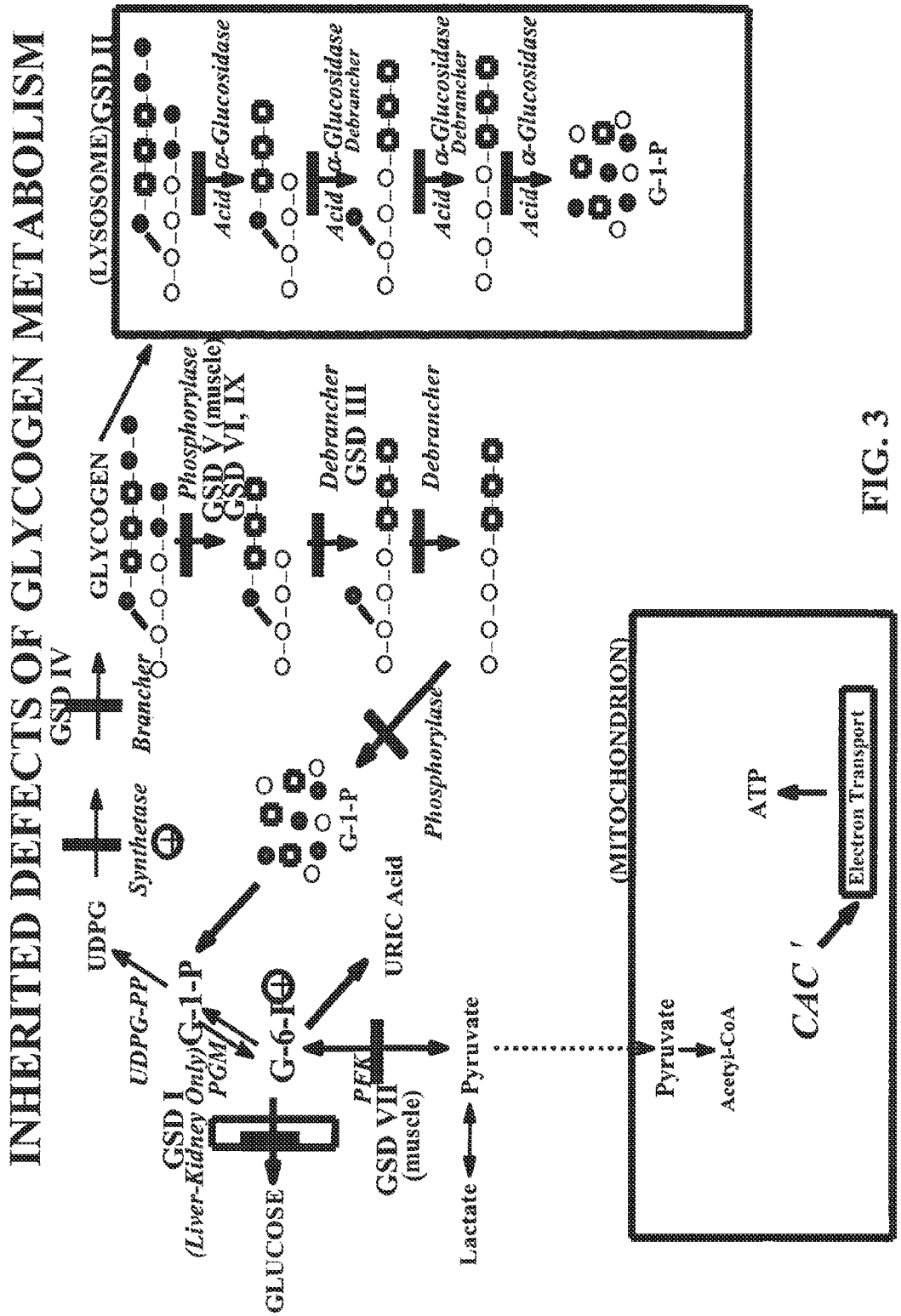
FIG. 3 is a schematic drawing depicting the possible enzyme deficiencies in inherited defects involving glycogen metabolism in humans. (GSD I-GSD VII)

Now referring to FIG. 3, the (red) bars show the location of the various inherited deficiencies causing Glycogen Storage Disease in humans. If any of these defects are present, it affects the ability of the subject to receive adequate energy from stored glycogen or polysaccharide. See: Chen, YT: Glycogen Storage Diseases. In: The Metabolic and Molecular Bases of Inherited Diseases, 8th edition, Chapter 71, pp 1521-1551, Mc-Graw-Hill, 2001.

Figure 4:
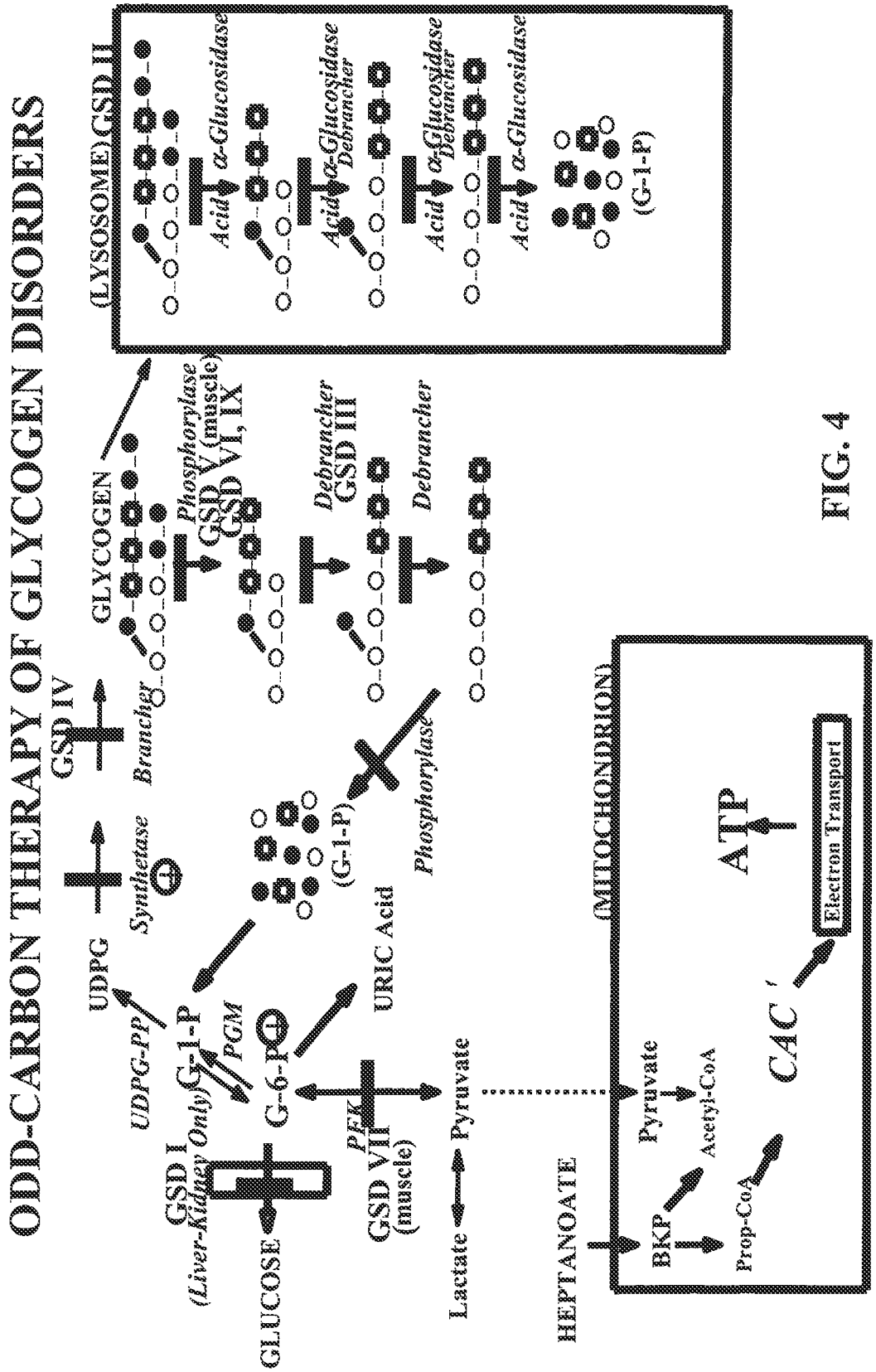
FIG. 4 is a schematic drawing depicting the effect of odd-carbon therapy on glycogen metabolic disorders, including GSD II, in humans.

FIG. 4 shows how odd-carbon therapy serves to circumvent the problems of glycogen metabolism that may be present. Administration of odd-carbon fatty acids (for example as triglycerides or as acids such as heptanoate) provides an alternate energy source, in the form of intramitochondrial acetyl-CoA and Propionyl-CoA, that can be utilized directly by the Krebs or "citric acid" cycle regardless of the existence of any one of the defects of glycogen metabolism (shown as red bars). Therefore, the demand for energy from glycogen is eliminated.

FIG. 5 is a graph that shows the effect of a triheptanoin-containing diet on the levels of select amino acids in an adult onset glycogen storage disease—Type II patient (GSD II or Pompes' Disease) following treatment with the Triheptanoin diet. The characteristic deficits of Alanine and Glutamine were restored within 13 hours with only the Triheptanoin diet, which documents the rapid elimination of the need for degradation of body muscle protein by provision of energy from Triheptanoin. The rapid reduction of the serum levels of these amino acids is obvious when the source of Triheptanoin was interrupted (NPO) awaiting the placement of a gastrostomy tube. Following that event and the resumed delivery of Triheptanoin via the gastrostomy tube, these serum amino acids were rapidly restored to normal.

Figure 6:
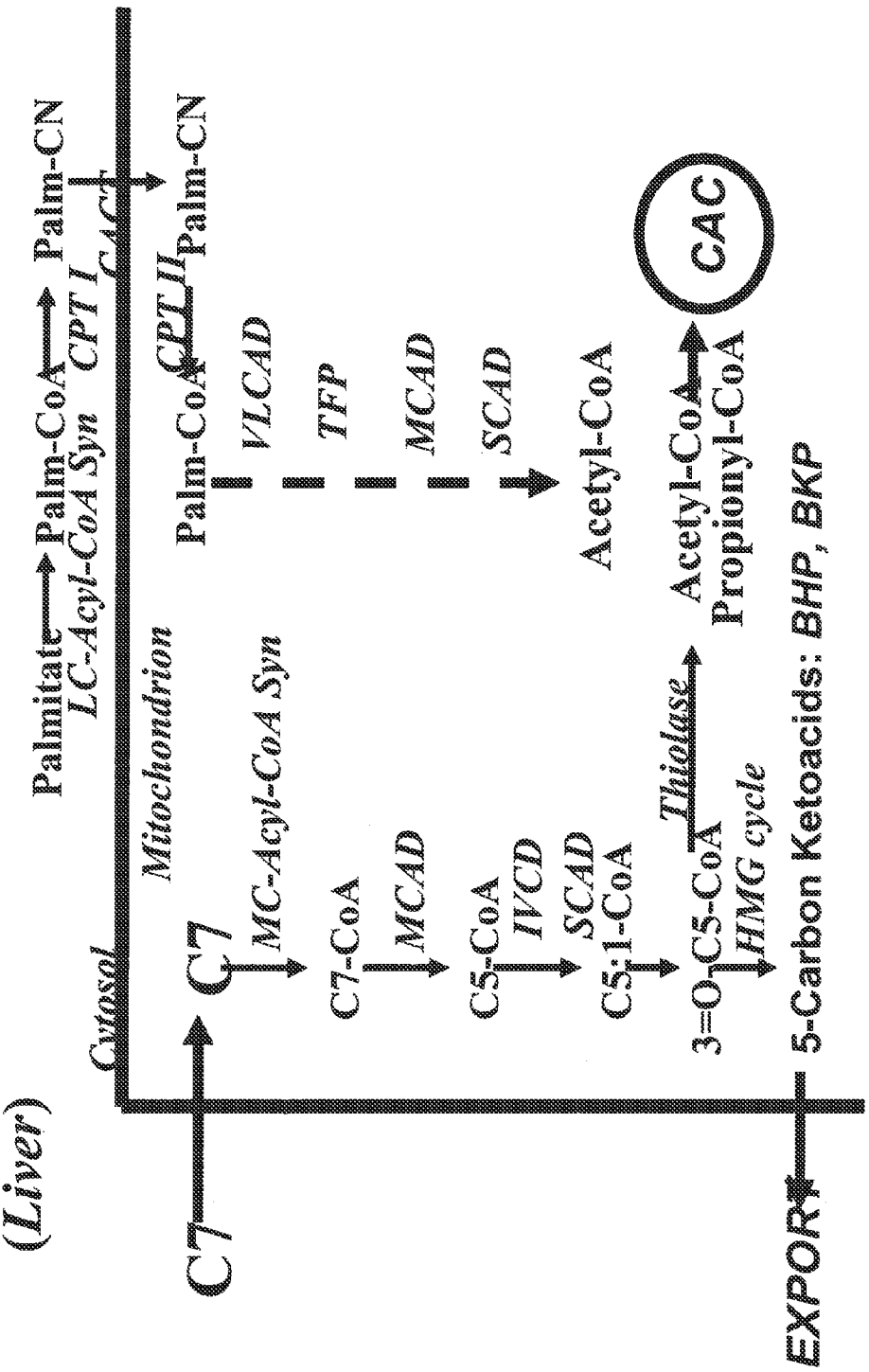
FIG. 6 is a diagram that shows the oxidative sequence for heptanoate (liver)
Figure 7:
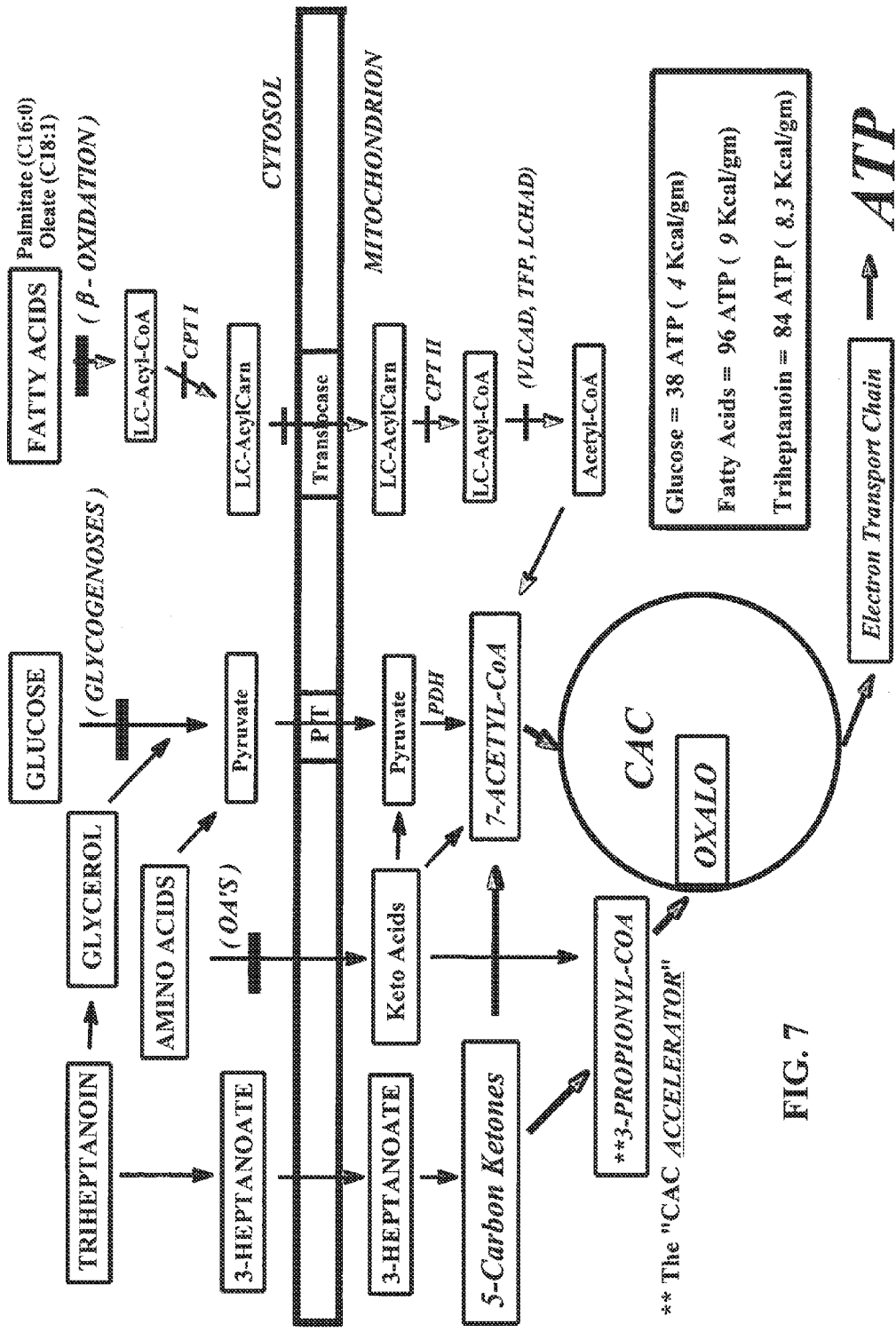
FIG. 7 is a diagram that shows the entry points in metabolism, e.g., in the CAC of the odd chain fatty acids of the present invention.
Figure 8:
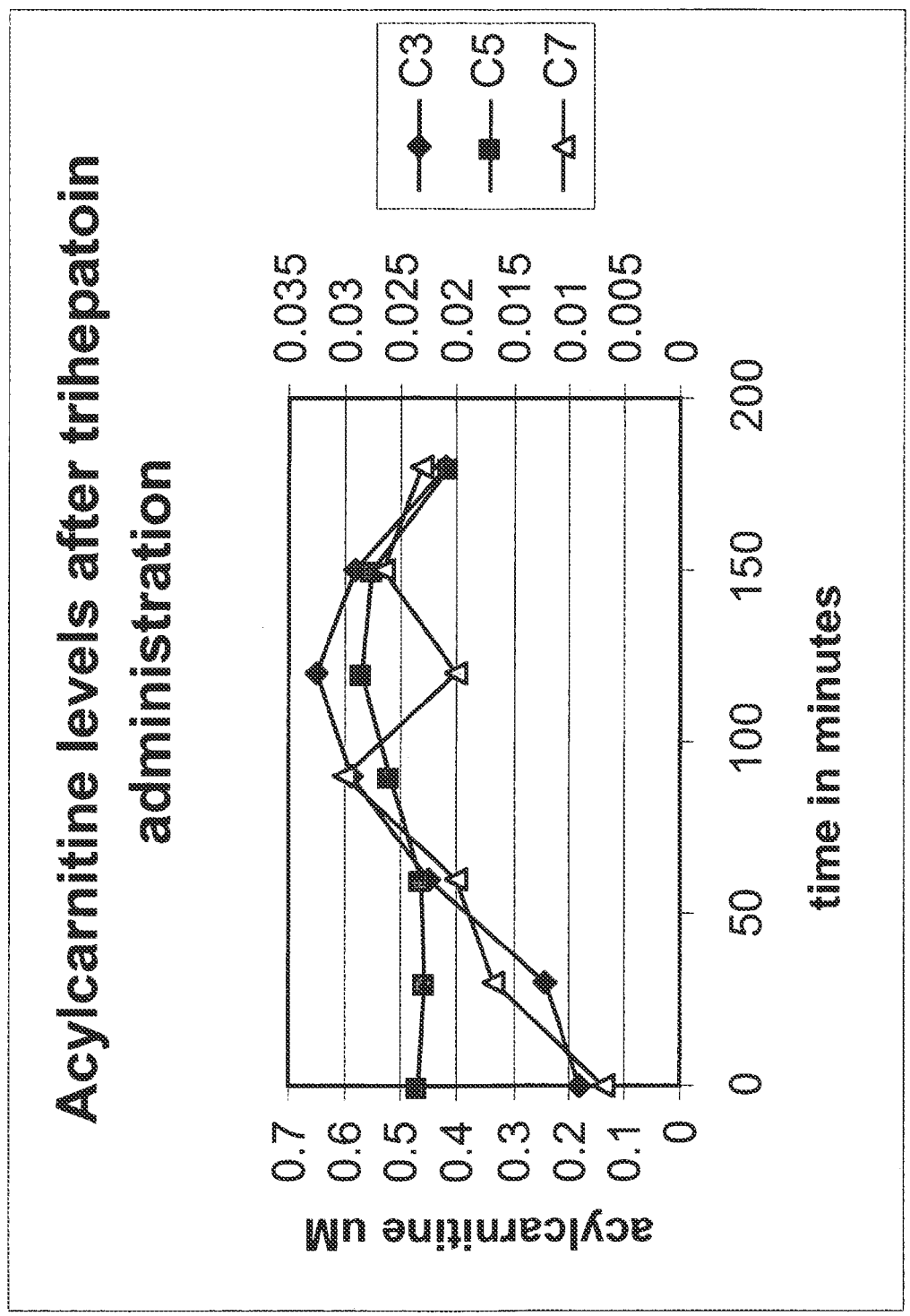
FIG. 8 is a graph that compared the acylcarnitine levels after trihepatoin treatment in horses.

FIG. 6 shows the steps and location of, e.g., C7 metabolism. The abbreviations on the right hand side of the arrows shows the location of various FODs that are mitigated and/or avoided using the odd chain fatty acids of the present invention as a single source of fats or as a supplement. FIG. 7 summarized the "CAC acceleration" of the present invention. By providing additional C2-CoA and C3-CoA into the CAC, the odd chain fatty acids of the present invention circumvent and avoid the enzymes that are deficient or lacking in FOD patients. Importantly, the odd chain fatty acids of the present invention may be provided as an adjunct to current enzyme replacement therapies, e.g., intravenous PEGylated-α-glycoside or other like enzymes. By providing additional support for patients, a larger pool of patient may be addressed, with reduced cost, increased compliance, reduced morbidity and mortality and increased patient satisfaction.

The odd chain fatty acids of the present invention not only prevented lipolysis they were also found to eliminate chronic infections in FOD patients. To spare intra-mitochondrial Coenzyme A, simple carnitine supplementation is required. Importantly, it was found that the odd chain fatty acids optimized the supply of propionate and acetate to the CAC and augmented ATP Production. Furthermore, unlike the use of supplemental propionate, the present invention did not sterilize the gut. The present invention provides a readily available energy source via an alternate pathway and may even be used to evaluate and protect siblings from disease.

The basic principle of the alternative metabolic pathway of the present invention is to reduce the need for carbohydrate in the form of stored glycogen or polysaccharide as substrate for the Citric Acid (Kreb's) Cycle (CAC). Meeting the energy needs of the body with Triheptanoin or other odd carbon fatty acids (C15, C5 or BHP) can permit the gradual reduction of excessive stored glycogen or polysaccharide resulting from any of the various types of glycogen storage disease. This is accomplished by the intact alternate metabolic pathway for glycogen degradation that exists in either the cytosol and in the lysosome. Patients with GSD II must remain on a diet containing odd carbon fatty acids, daily, for life, in order to prevent further occurrence of the clinical complications of the disease.

The amount of odd carbon fatty acid or ketone to provide is 25-35% of total Kcal/day for humans and ~10-20% of total Kcal/day for horses and other animals. The amount given can be calculated based on the weight of the patient in kilograms (Kg). The effective dose for adult humans and horses when triheptanoin is utilized, for example, is 1-2 gm/Kg/day. The dose for children when triheptanoin is utilized is approximately 1 to 4, preferably 3-4 gm/Kg/day.

The odd carbon fatty acid or ketone may be administered enterally or parenterally. Enteral administration includes oral administration and administration via a nasogastric tube or via a gastrostomy tube. The administered substance may be in a food or beverage or a nutritional composition. It may be desirable to control or monitor the total caloric intake of the subject and this may be accomplished through preparation of an appropriate liquid diet. A parenterally administered preparation may be made by methods known in the art for adding fatty acids as triglyceride emulsions to parenteral nutritional preparations.

For horses as well as such animals as cattle and sheep, one may use from about 1-2 gm/kg/day of triheptanoin and sufficient amounts of any other odd carbon fatty acid or ketone to provide about 10 to 20% of the total Kcal/day. The dose must be maintained at the optimal level related to Kg body weight for the best therapeutic result. This is especially important for a young growing animal or human child. Symptoms return when the dose per kg/day decreases as a result of growth and weight gain. It can be given to animals in a variety of ways, as with humans. It can be mixed with liquids, given straight via tube, or absorbed into "feed pellets" like "alfalfa" or other animal feeds. Parenteral therapy for animals is not a frequent treatment approach at this time, but it could be used very effectively with horses and other large animals when illness or stress results in serious metabolic crisis.

Organic Acids may be measured as follows. Organic acids in urine specimens are determined with isolation by Liquid Partition Chromatography (LPC) and quantitative Gas Chromatography-Mass Spectrometry (GCMS) using an internal standard. The specimen is derivatized to form pentafluorobenzyl oximes (PFBO) of oxo-acids and the organic acids isolated by Liquid Partition chromatography on silicic acid hydrated with dilute sulfuric acid and eluted with mixtures of tert-Amyl alcohol and chloroform. After drying, the organic acids are derivatized to form volatile trimethylsilyl (TMS) derivatives for separation by capillary Gas Chromatography (GC) with temperature programming. Detection is by Mass Spectrometry (MS) with identification of the organic acids by their mass spectra. Organic acids are quantified by peak areas of reconstructed ion chromatograms with internal standards and calibration curves.

Acylcarnitine Profiles. Acylcarnitines and carnitine levels in dried blood spots (dbs), plasma and amniotic fluid by automated electrospray tandem mass spectrometry Acylcarnitines are extracted from blood spots, plasmas and amniotic fluid with methanol containing stable isotopically labeled internal standards. The extract is derivatized to form butyl esters. An automated sample introduction system delivers the samples to the electrospray tandem mass spectrometer (ESI-MS/MS) operating in the multiple channel analysis mode in which acylcarnitines are identified, profiled, and quantified with stable isotopically labeled internal standards. This test also provides quantification of free, sum of acylcarnitines, and total carnitine levels.

EXAMPLE 1

Treatment of Human Subject Diagnosed with Acid Maltase Deficiency

Clinical Description. A 42 year old caucasian female had onset of progressive muscle weakness and difficulty breathing dating back nearly 20 years. She was seen at 40 years for muscle weakness and a muscle biopsy revealed increased glycogen deposition in lysosomes and cytosol (2.0%–normal 1.03+/−0.18%), autophagic vacuolization, and increased acid phosphatase staining An assay for acid-α-glucosidase confirmed the deficiency as adult-onset GSD II (0.46—normal 8.13+/−2.1 nm MU-hydrolyzed/min/gm). No therapy was initiated.

During the subsequent 2 years, the patient experienced progressive muscle weakness, affecting strength and endurance, swallowing and producing urgency for urination and defecation. The patient's breathing became a major issue and weight had decreased from ~127 to 101 lbs (46 Kg) over this interval. Pulmonary evaluation a day prior to admission revealed MIP=−70 cm HOH; MEP=+60 cm HOH; FVC=40% of predicted (1.4 liters); blood gases: pH 7.38, $pCO_2$ 68, $pO_2$ 56 (room air). Home $O_2$ was started and upon respiratory arrest was intubated and unsuccessfully extubated leading to emergency admission lasting one month. Following informed consent, the patient agreed to enter an approved Institutional Review Board (IRB) Protocol for dietary therapy with triheptanoin oil.

Clinical and Biochemical Course on Therapy. The patient was admitted with left lower lobe atelectasis and infiltrate, placed on antibiotics, carnitine supplement (20 mg/Kg/day) and diet containing triheptanoin was given by nasogastric tube. Esophageal dysmotility was documented. A percutaneous endoscopic gastrostomy (PEG) was placed on the sixth hospital day.

The diet was based on vivonex and ~1500 Kcal was given by nasogastric tube, on admission. The composition (% Kcal) was: Protein 29%, carbohydrate (CHO) 30%, total lipid 41% (of which triheptanoin (C7) accounted for 26%). The C7 dose of 1 gm/Kg/day (8.3 Kcal/gm) was gradually raised from 26% to 35% and finally 40% of total Kcal corresponding to 1.0, 1.5, and 2.0 gm C7 per Kg per day. Carbohydrate was correspondingly reduced from 30 to 27 to 11% of total Kcal/day. Total caloric intake was raised from ~1500 to 1700 to 1900 per day with these dietary changes during her 33 day admission.

Within 13 hours of beginning the C7 diet, $pCO_2$ fell from 68 to 43 (normal 35-45), and a long history of urgency for urination and defecation had ceased and remained normal for the rest of the admission. The patient began ambulating by the 10th day that improved steadily, showering with assistance by the 28th day. Pneumonia on day 17 responded to therapy and was extubated on day 23. She was discharged on bilevel positive airway pressure (BIPAP), the C7 diet, and carnitine supplement.

Following discharge, the patient returned to work half-time at 5 weeks and was working full-time by 10 weeks. Swallowing was sufficiently improved that gastrostomy feeds were stopped at 7 months and the PEG was removed at 10 months. By 15 months post-discharge, patient weight had increased from 46 Kg on admission to 60 Kg and has remained stable. Patient maintains normal activities without any significant weakness but continues to use BIPAP at night. Patient $pCO_2$ levels remain in the normal range, however, her full vital capacity remains at 40-45% of predicted.

Metabolic Observations. Routine blood chemistries on admission were largely normal except for $pCO_2$ of 68.1 (normal 35-45 units). ALT and AST and LDL were mildly elevated while serum CPK was normal. Hemoglobin was 11 gm/dl and creatinine was reduced slightly at 0.4 (normal 0.5-1.0). Urinalysis revealed ketosis. Potassium was reduced, slightly (3.5, normal 3.6-5.0 units). Blood acylcarnitine analysis revealed normal total carnitine with increased acetycarnitine (ketosis), and a surprising decrease in propionyl-carnitine (1.25, normal <2.71 uM). There were no other acyl-carnitine abnormalities.

Quantitative urinary organic acids revealed only ketosis with a urine pH=8.5. The excretion of 3-OH-butyrate (BOB) and acetoacetate (AcAc) was 1633 and 1211 mmol/mol creatinine, respectively, (normal: <17 & 7 respectively). The ratio of BOB:AcAc was decreased from 2.4 to 1.3 suggesting an alteration in the intra-mitochondrial redox state. During hospitalization and follow-up, this ratio was less than 1.17 (range 0.40-1.17) during 4 of 5 episodes of mild to moderate ketosis. However, more recently with addition of an amino acid supplement to the C7 diet, the levels and ratio became normal (3.0). Citric acid cycle intermediate excretion fell into the normal ranges for adults.

The most significant abnormalities were observed with plasma amino acid analysis. The levels of Alanine and Glutamine were low compared to the adult normal ranges. While the levels of the branched-chain amino acids (BCAA=Leucine, Valine, & Isoleucine) were within the adult normal ranges. The reduced levels of Alanine and Glutamine have been observed often in this disease and has led to the high protein—low carbohydrate diet and/or alanine supplementation. This patient did not receive any supplementary alanine. In only thirteen hours after initiating the C7 diet by nasogastric tube, the plasma alanine level had increased 4-fold. Glutamine increased nearly 2-fold as did the branched chain amino acids (BCAAs). The levels of these amino acids remained in the normal range while receiving the C7 diet. However, the diet was interrupted on day 4 & 5 while awaiting placement of the PEG for gastrostomy feeding. The levels of each of these amino acids promptly fell to admission levels (Table 2: 65 & 84 hour samples). With resumption of the diet via gastrostomy, all levels returned to (or above) the normal ranges in 24 hours. These amino acid levels remained normal on this odd-carbon triglyceride diet therapy. Further analysis of all of the measured amino acids revealed the same sudden increase with the C7 diet and the same sudden decrease when the diet was interrupted. As C7 was increased from 26 to 40% of total caloric intake (from 1.0 to 2.0 gm/Kg/day). All amino acids remained normal and propionylcarnitine levels had increased without any evidence for propionyl overload from the metabolism of heptanoate.

Furthermore, the present invention may be used to provide a viable source of energy to patients with compromised ketogenesis, gluconeogenesis and even the urea cycle, due to FODs. The odd chain fatty acids help support the sub-optimal function of the Citric Acid Cycle, gluconeogenesis, the urea cycle and ATP generation by the respiratory chain. The anaplerotic substrates support the Citric Acid Cycle, e.g., by providing pyruvate to malate and oxaloacetate; glutamate to ketoglutarate and heptanoate to propionyl-CoA to succinyl-CoA. These types of support may be provided alone or in combination. Furthermore, the present invention may be used with, e.g., amino acid supplementation to reduce or prevent amino acid scavenging as an alternative source of energy. As the patient improves, muscle and other tissues require additional amino acid support, which may be supplemented along with the present invention using amino acid supplements. One example of an amino acid supplement for use with the present invention is Amino-Vital, which contains branched chain amino acids (BCAA) via branched chain ketone acids (BCKA) that may also supplement the C2-CoA and C3-CoA. Additional co-factors and vitamins (e.g., Biotin and B-12) may be added to the patient's diet to improve the metabolism of Propionyl-CoA to Succinyl-CoA and/or entry into the CAC as Acetyl-CoA.

EXAMPLE 2

Treatment of Human Subject Diagnosed with GSDII

Clinical History & Description. A 66 year old white male whose history of muscle weakness dated back to his youth when he noticed weakness that caused limitations in sports activities. In his 40's, he became much more aware of weakness that primarily affected his back and legs. Spirometry, at that time, revealed reduced lung capacity. At age 54, a muscle biopsy was obtained that showed glycogen deposition in lysosomes and cytoplasm but was not increased (0.76%). Acid maltase was 0.94 (normal: 8.13+/−2.1). Debrancher enzyme was also assayed in this biopsy and was 1.40 (range 1.88-4.24). Shortly after that, he experienced shortness of breath at high altitude and has used bilevel positive airway pressure (BIPAP) since that time also for sleep apnea. Patient muscle weakness was progressive and he has been using a motorized scooter for the past 10 years. Patient weakness was generalized, he had great difficulty standing, and walked with an irregular gait, using a cane. Patient had no history of impaired swallowing but did complain of urgency for urination and defecation.

Clinical Course. Following informed consent, the patient agreed to enter an approved IRB Protocol for dietary therapy with triheptanoin oil. Initial pulmonary studies revealed severe restriction of his vital capacity (2.41 L, 43% of predicted). Maximal inspiratory and expiratory pressures were 60 cm of water. Initial arterial blood gases revealed pH=7.39, $pCO_2$=51. And $pO_2$=62.

The oral diet consisted of 2900 Kcal on admission. The composition (% Kcal) was: Protein 16%, carbohydrate (CHO) 40%, total lipid 44% (of which triheptanoin (C7) represented 22%). The C7 dose of 1 gm/Kg/day (8.3 Kcal/gm) was gradually raised from 26% to 30% of total Kcal corresponding to 1.0, and 1.5, gm C7 per Kg per day. Carbohydrate was correspondingly reduced from 43 to 22% of total Kcal/day. Total caloric intake was maintained at ~2800 per day during his 30 day admission.

Initially, the patient required assistance and supervision with grooming, upper and lower extremity dressing, bathing, and toileting. The patient also required maximal assistance with ambulation and transfers from bed to wheelchair. With intensive physical therapy and diet, at discharge, he had became independent with grooming, upper and lower extremity dressing, toileting, and locomotion with a manual wheelchair. He continued to require supervision, but without assistance, with transfers from bed to wheelchair and to toilet and shower. He had clearly made improvements in strength and endurance with exercise. Pulmonary function testing showed an increase of 700 ml in total vital capacity when compared to his studies on admission.

The patient was discharged on the triheptanoin diet with supplements of citrate (bicitra, 15 cc four times a day) and amino acid supplement ("Amino-Vital", Ajinomoto, Inc) 4.8 gms four times a day. At four months after discharge, he continues this regimen and physical therapy three times per week.

Metabolic Observations. Routine blood chemistries on admission were largely normal except for $pCO_2$ of 51 (normal 35-45 units). ALT and AST and lipid profile were normal while serum CPK was mildly increased (218, normal: 38-174 IU/L). His BUN was increased (30, range 9-20 units) and creatinine was reduced slightly at 0.6 (normal 0.7-1.2 units). All other chemistries were normal. Blood acylcarnitine analysis revealed normal total carnitine and a reduced level of propionylcarnitine (1.08, normal <2.71 uM). There were no other acylcarnitine abnormalities.

Patient diet was initially adjusted to 2800-3000 Kcal/day composed of protein 16%, CHO 40%, total lipid 44% of which C7 represented 22% of his daily Kcal intake. The C7 composition was increased to 30-31% during the admission. His initial response to C7 reveled a marked decrease in urinary pH (from 7.5 to 6.0) and acylcarnitine monitoring revealed a marked increase in propionylcarnitine (1.08 to 5.86 uM) and pimelate, heptanoate and methylmalonate (MMA) excretion increased significantly (321, 307, and 38 mol/mol creatinine, respectively. These changes indicated impaired oxidation of C7 and reduced utilization of propionyl-CoA for the citric acid cycle (CAC). Following supplementation with citrate (bicitra) the urine pH returned to 7.5, and pimelate, heptanoate, and MMA decreased immediately to 58, 50, and 24, respectively. The propionylcarnitine blood level was also reduced to 3.74 uM. These changes reflected more normal metabolism of dietary C7. Citrate supplementation was continued throughout the treatment.

Although there were 5 periods when the quantitative urinary organic acids revealed mild ketosis, the ratio of BOB:AcAc was always normal while on citrate supplementation. Unlike patient 1, there was no indication of an alteration in the intra-mitochondrial redox state. Although citric acid cycle intermediate excretion was in the normal adult ranges, there were some abnormalities: isocitrate was initially increased (134–n1=<82) while succinate and a-ketoglutarate levels were reduced (6 [n1<42], and 4 [n1<75], respectively. The sum of the excretion of the CAC intermediates was 391 (upper limit=1185). This profile persisted during the study.

The most significant abnormalities were observed with plasma amino acid analysis. The levels of Alanine and Glutamine were low compared to the adult normal ranges. While the levels of the branched-chain amino acids (BCAA=Leucine, Valine, & Isoleucine) were within the adult normal ranges. The reduced levels of Alanine and Glutamine have been observed often in this disease and has led to the high protein—low carbohydrate diet and/or alanine supplementation. This patient did not receive any supplementary alanine. In only thirteen hours after initiating the C7 diet by nasogastric tube, the plasma alanine level had increased 4-fold. Glutamine increased nearly 2-fold as did the BCAA's. The levels of these amino acids remained in the normal range while receiving the C7 diet. However, the diet was interrupted on day 4 & 5 while awaiting placement of the PEG for gastrostomy feeding. The levels of each of these amino acids promptly fell to admission levels. With resumption of the diet via gastrostomy, all levels returned to (or above) the normal ranges in 24 hours. These amino acid levels remained normal on this odd-carbon triglyceride diet therapy. Further analysis of all of the measured amino acids revealed the same sudden increase with the C7 diet and the same sudden decrease when the diet was interrupted. As C7 was increased from 26 to 40% of total caloric intake (from 1.0 to 2.0 gm/Kg/day). All amino acids remained normal and propionylcarnitine levels had increased without any evidence for propionyl overload from the metabolism of heptanoate.

EXAMPLE 3

Treatment of Horses. Three horses affected with biopsy proven, polysaccharide storage myopathy have been successfully treated with the triheptanoin diet. The first was an 8 year old mare who was unable to walk or exercise without severe muscle pain, rhabdomyolysis, and "locking up." The owners were approaching "putting the animal down" (killing it). Within 30 days of triheptanoin diet incorporated into feed pellets, this animal has become asymptomatic and has returned to full training and riding without any symptoms.

A second horse was encountered at 4 months with proven polysaccharide storage myopathy (PSSM) that was not able to walk adequately or nurse from its mother. The owners were prepared to kill the animal but decided to try the triheptanoin diet first. Within 24 hours of initiating the triheptanoin diet, the foal was running and playing with other young horses without any evidence of muscle pain, etc. All blood enzyme levels related to muscle disease (including serum creatine phosphokinase) had normalized. As this foal gained weight, in a normal rate for a young horse, symptoms returned since the dose of C7 had not been adjusted for the weight gain. Adjustment of the dose back to 2 grams/Kg body weight eliminated all symptoms and there is no further evidence of disease.

A third horse, also an 8 year old mare, developed PSSM and "locked up." She was no longer available to ride and could no longer jump. She started triheptanoin at 1.0 gm/Kg/day added to her diet pellet feeds and is currently asymptomatic with normal blood chemistry levels compared to pre-treatment after only one week of diet treatment.

EXAMPLE 4

Treatment of FOD in Horses and Diets for Treatment of Fatigue

Figure 9:
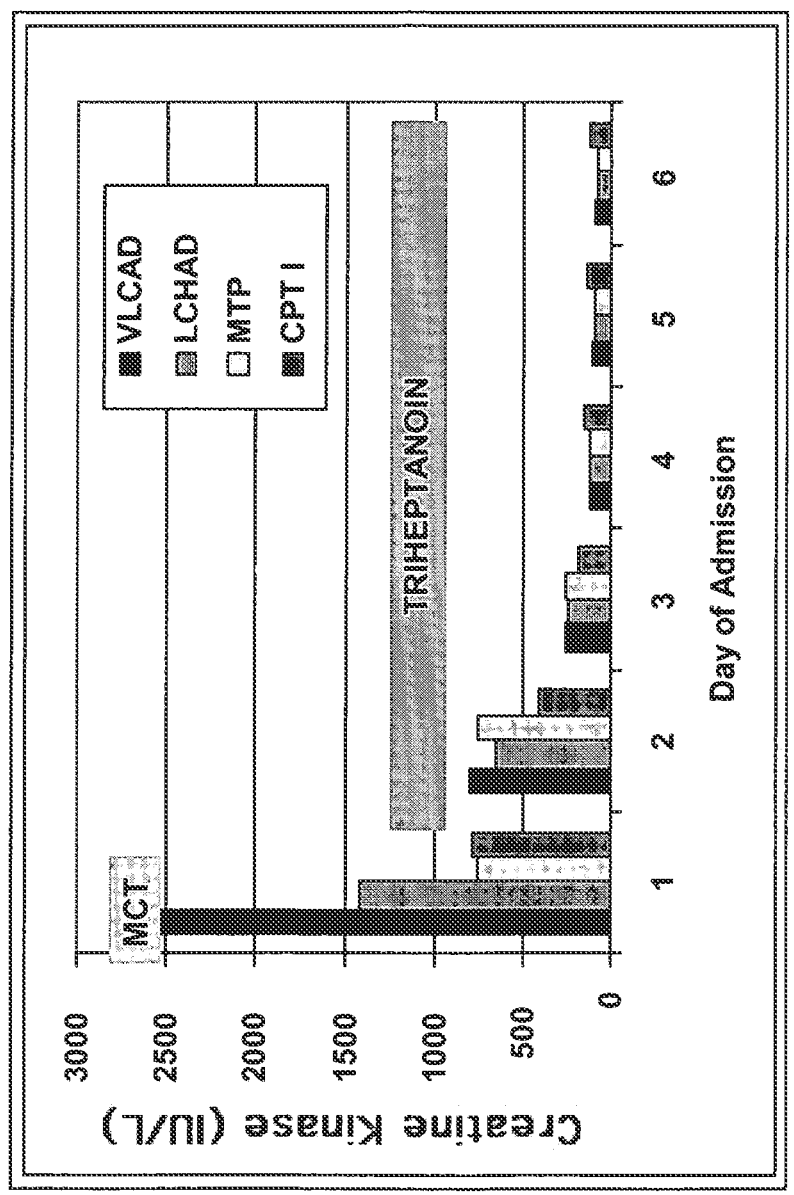
FIG. 9 is a graph that shows the effects of a resolution of rhabdomyolysis with dietary triheptanoin in various types of FODs.

Horses: Eight healthy, fit 4 year old thoroughbred geldings may be used in a study. These horses are all sound and trained to the treadmill. The ability of horses to absorb and digest C7 oil was first determined. Three horses were fasted for 12 hours prior to administration of 0.5 gm/kg of triheptanoin via nasogastric tube. Samples for blood acylcarnitine profile were drawn at 30, 60, 90, 120, 150, and 180 minutes after triheptanoin administration. C7 acyl carnitine peaked at 90 minutes after administration and peak serum concentration of C5 and C3 acylcarnitines occurred 120 minutes after administration (FIG. 9).

In humans C7 (triheptanoin) is hydrolyzed to heptanoate which is then oxidized in the liver to form β-hydroxypentonate and β-ketopentonate, both 5 carbon ketone bodies (C5). C5 is metabolized to C3 (propionyl CoA) and C2 or acetyl CoA. These fatty acids are transported in the bloodstream as acylcarnitines, which are easily taken up in muscle tissues and cross mitochondrial membranes to enter the CAC.

The five carbon ketones β-hydroxypentonate and β-ketopentonate produced from the breakdown of triheptanoin in the liver are represented in our preliminary results as plasma C5 acylcarnitine. Horses have a poorly developed ability to produce ketone bodies, however the presence of 5 carbon acylcarnitines in our horses, suggests that they were able to metabolize triheptanoin into the 5 carbon ketone. C3 acylcarnitines were also increased in our preliminary studies suggesting the break down of the C5 to propionyl CoA (C3).

Palatability of C7 has also been studied, in which the C7 was provided as triheptanoin or mixed with corn oil into the diet of horses. It was found that when horses were fed the oil mixed into hay cubes soaked in water prior to feeding, they consistently ate all of the feed.

Diets: A variety of diets may be formulated. For example, the diets may be isocaloric and formulated to meet the minimum daily requirements for all nutrients. In one example of horse feed is made that includes 8.5 kg of grass hay/grass hay cubes, 0.5 kg of ration balancer, free choice salt and 750 mls of oil per day with a total digestible energy of 23 MCal/500 kg horse per day. The oil will be either triheptanoin (provided by Dr. Roe) or corn oil (purchased) and will be divided into 3 feedings.

Exercise study: Horses will generally be rested for one day prior to and one day after the exercise study. On day 14 of each diet an IV catheter will be placed and horses will perform a 90 min submaximal exercise study on a flat treadmill 120 min after consuming the oil. A loosely fitting mask with a high flow rate may be placed over the horse's nose and samples of expired gas collected every 15 minutes during exercise using an open circuit calorimeter. Oxygen consumption ($VO_2$) and carbon dioxide production ($VCO_2$) will be measured and respiratory exchange ratio (RER) will be calculated.

The exercise study protocol may include a 5 min warm up at a walk, followed by:
Block 1: 15 min 35% $VO_2$ max (previously measured in these horses), 5 min walk
Block 2: 15 min 35% $VO_2$ max, 5 min walk
Block 3: 15 min 35% $VO_2$ max, 5 min walk
Block 4: 15 min 35% $VO_2$ max, 5 min walk
Block 5: 10 min 75% $VO_2$ max
Block 6: 5 min walk Blood samples: Blood samples may be drawn prior to the initiation of the trial; prior to the exercise study; and at the end of the highest speed during each exercise block of the exercise study. Blood samples for glucose, lactate, ketones, FFA, amino acids and acylcarnitine concentrations will be obtained. Glucose and lactate will be assayed on an automated lactate analyzer and ketones and FFA will be assayed spectrophotometrically using the appropriate kits. Plasma amino acid and aclycarnitine levels may also be measured by mass spectrometry from four randomly selected horses; all other values will be analyzed in all study subjects.

Muscle Biopsy: Gluteal muscle biopsy specimens may be obtained by use of a percutaneous needle biopsy technique prior to initiation of the diet trial; prior to and immediately upon completion of the exercise study; and 24 hours after exercise study. Samples are obtained within a 2 inch square at a standardized site along the gluteal medius muscle and alternating sides will be used for each sample. Biopsy specimens will be immediately frozen in liquid nitrogen and stored at −80° C.

Muscle Analysis: Frozen muscle specimens will be dissected free of blood and connective tissue. Glycogen will be assayed flourometric as glucose residues remaining after 1-2 mg portions of muscle tissue are boiled for 2 h in 1 M HCl. Lactate, pyruvate, G-6-P, and CAC intermediates will be assayed in a separate portion of the muscle sample (8). One 4 mg portion of muscle will be homogenized by crushing with a glass rod in 1.5M perchloric acid. The supernatant obtained after centrifugation will be neutralized with $KHCO_3$, centrifuged again and the remaining supernatant removed for analysis of metabolites using fluorometric techniques and purine nucleotides using high-performance liquid chromatography (HPLC). Concentrations of CP, ATP, ADP, AMP and IMP in muscle specimens as well as in external standards will be analyzed by use of a reverse phase column (10). Separation of nucleotides will be achieved with a flow rate of 1.0 mL/min, UV-detection at 254 nm, and an oven temperature of 40° C.

Urine Samples: A urine collection device is placed the evening prior to exercise on the 4 horses randomly selected for plasma acylcarnitnies and amino acid analyses and will again be placed on the horses after exercise. An aliquot of voided urine will be collected for measurement of urine organic acids by mass spectrometry.

EXAMPLE 4

Beverages and Food Supplements. In one embodiment, the odd chain fatty acids of the present invention may be provided as a nutritional supplement and/or as part of an overall patient diet. As a non-limiting example of a foodstuff that may include the present invention in a pharmaceutical or nutritional amount, the odd chain fatty acids may be formulated into a snack bar, such as that described in U.S. Pat. No. 4,777,045, issued to Vanderveer, relevant portions incorporated herein by reference. A high bran snack is taught that includes a typical formulation of graham (whole wheat) flour, 40 percent; rice flour, 10 percent; whole wheat bran flour, 50 percent; calcium carbonate, 1.25 percent; reduced iron, 0.013 percent; and riboflavin (as a tracer), 0.02 percent and between 0.1 and 10% odd chain fatty acids. Water is added per 80 ounces of dry materials to provide a semi-solid flowable product that may be fed into a ribbon blender and then into a cooker extruder, e.g., a twin-screw cooker extruder. Each of the ingredients in the formulation has a processing, nutritional or therapeutic purpose. The extruded pieces may be further flavored, e.g., coated with coconut oil and powdered flavorant.

A whole wheat and bran snack may be 50 weight percent of wheat bran, with approximately 50 percent of whole wheat flour, including 0.2 weight percent of riboflavin (20 mg per 100 gm of finished product), have a desired size, density and shape for the subsequent operation of adding oil, flavor and eventually packaging. Samples of finished products, with 4 different flavors, applied at a level of 3 weight percent to the extruded base product, with the addition of 3 weight percent of odd chain fatty acids. The extent and formulation of the odd chain fatty acids (e.g., with an emulsifier) may improved adhesion of the flavor particles, flavor acceptability and mouth feel organoleptically. The bar may further include vitamins, minerals and even protein and carbohydrates to provide a so-called "power-bar."

Another bar may be a granola bar with supplemental dietary fiber as taught by Linscott in U.S. Pat. No. 4,871,557, relevant portions incorporated herein by reference. A granola bar is taught that includes supplemental dietary fiber added to the granola bar in the form of compressed flakes, as well as the method of making such a granola bar, which may further include the odd chain fatty acids of the present invention. Briefly, a mixture of granola ingredients such as grains, fruits, nuts and compressed flakes are mixed with the granola ingredients and the odd chain fatty acids. The compressed flakes of supplemental dietary fiber are combined with water and a binder material, such as rice flour, and then extruded. The extrudate is dried and then ground to the desired particle size.

Although sources of supplemental dietary fiber can contribute both soluble and insoluble fiber, sources generally known to contribute insoluble fiber include but are not limited to soy fiber, apple fiber, corn bran, wheat bran, oat bran, barley bran, rye bran, triticale bran, cellulose, pea fiber, sugar beet fiber, and peanut fiber. Sources generally known to contribute soluble fiber include but are not limited to gum arabic, gum ghatti, guar gum, pectins, psyllium, carrageenans, xanthan, tragacanth, karaya, locust bean gum, agar, and alginates. These non-digestible fibers provide additional control over the exact amount of kilocalories are provided to a patient as the primary source of energy from fat is provided by the odd chain fatty acids.

The extrusion step may be performed by conventional techniques in conventional extrusion apparatus, e.g., a damp mixture is heated to a temperature between about 300 and about 330° F., e.g., 315° F. during the extrusion process. The damp mixture is then extruded at a pressure of between about 100 and about 900 p.s.i. A die through which the mix is extruded may includes a square, rectangular, triangular, oval or round hole with a diameter of, e.g., 0.5 inches. Generally, extrudates are particle sized before being dried in an oven at 270° F. for about 20 minutes. Often, the dried particles will have a moisture content of about 7 percent.

The odd chain fatty acids may also be provided as beverage. The odd chain fatty acids may be added to a beverage such as that taught in U.S. Pat. No. 4,981,687, relevant portions incorporated herein by reference. The beverage taught is used to improve physiological responses to exercise, however, it uses standard sources of carbohydrates. The addition of the odd chain fatty acids taught herein provides a beverage that not only reduces or prevents adverse physiological effects of physical exercise or environmental exposure, but provides a new and/or additional sources of readily available energy. The fluid will generally include water, electrolytes, and odd chain fatty acids and is non-toxic to man or animals. Sugar may also be provided or sugar substitutes may be used without a concomitant loss of new energy production. As such, the odd chain fatty acids substitute the energy source and can be absorbed rapidly through the gastrointestinal tract, prevents decreases in blood volume.

The odd chain fatty acids will provide a beneficial physiological effect on cells during exercise by providing a substitute and/or additional readily available energy source that may increase blood volume and cardiac output, improved skin blood flow, prevention or delay of onset of hyperthermia, increased rate of movement of electrolytes across the gastrointestinal wall, reduction in the breakdown of proteins and associated metabolism of essential amino acids, and decreased time needed for repair of body tissue following strenuous exercise.

When the fluid of the subject invention is administered, the body's physiological response to exercise or environmental exposure is greatly enhanced compared to the response when the body receives no fluids, receives only water, or receives fluid such as GATORADE®, which contains electrolytes and a sugar source in addition to water. The composition described here can be used to ameliorate the adverse effects of physical exertion or environmental exposure. The effect of the odd chain fatty acids on physical exertion may be measured by determining plasma volume, respiratory quotient, rectal temperature, pulse rate and/or cardiac output; combined with either enhanced endurance or performance, lower perceived difficulty of a physical task, or an enhanced ability to withstand heat exposure or chronic exposure to cold. The beverage may include: water, odd chain fatty acids (1-4%), potassium (2 meq/1), sodium (26 meq/1) and phosphate (4 meq/1).

Addition of a small amount of odd chain fatty acids, given at frequent intervals, may improve performance and endurance because it enhances entrance of both acetyl CoA and propionyl CoA into the Krebs cycle, thereby bypassing the need for additional oxaloacetate (OAA). The Krebs cycle is a well-known, but very complicated, biochemical pathway which provides a working muscle with its energy source. A detailed description of the Krebs cycle can be found in most biochemistry textbooks.

The beverage of the present invention may also be used to improve the physiologic response of any animal undergoing exercise or being subjected to high temperature conditions. For example, humans, horses, dogs, cats, mules, oxen, camels, emu, bison, nilguy, elephants, sheep, cows, chickens, turkey, goats, llamas, alpaca and pigs are a few of the animals that may benefit from the administration of the novel fluid composition described here. The fluid of the subject invention can also be used to alleviate or prevent dehydration which is known to result from chronic exposure to cold temperatures.

The odd chain fatty acids of the present invention may also be provided with dietetic beverages. An example of a dietetic beverage that may include the odd chain fatty acids includes, e.g., U.S. Pat. No. 4,042,684 that teaches a beverage for supplementing the dietetic requirements of sugar and essential salts in a mammalian body depleted through vigorous physical activity. The odd chain fatty acids may be added and substitute for simple carbohydrates in an aqueous that includes sodium chloride, potassium chloride, and free citric acid in physiologic ranges.

The combination of odd chain fatty acids and essential salts in a mammalian body will be particularly useful for athletes that have depleted short-term, immediately available energy through vigorous physical activity. For example, an athlete engaged in strenuous activity requires a ready source of energy for endurance, and replacement of both body fluids and essential salts lost through perspiration. Likewise, individuals working in a hot, humid atmosphere have similar requirements to maintain efficiency and productivity. Long term activity initiates bypass metabolism that the odd chain fatty acids of the present invention help to supplement to increase protein sparing.

Typical diets and sports beverages provide intake of sugars and sugar-precursor materials such as carbohydrates. When metabolized in the digestive tract, fuel values are obtained through enzyme and acid attack on these complex sugars. However, the process requires time to achieve the desired boost in metabolism, which is short lived and leads to protein and/or amino acid scavenging to supplement the citric acid cycle. Increased metabolic demands exceed the steady-state ability of this natural metabolic process.

Rather than rely on well-known sugar metabolism, e.g., fructose and glucose to achieve an energy store capable of providing needed fuel values, odd chain fatty acids provide the fully utilizable energy at the cellular level for metabolism in either the liver or muscles, brain, kidney and heart. One problem with commonly available sports beverages is that, e.g., glucose is easily and rapidly transported out of the digestive system into the blood whereas fructose is more passively and slowly transported. Once into circulation, the fructose is somewhat more efficient insofar as initial transport requires less energy and subsequent utilization for energy proceeds more readily. Thus, both immediate and longer lasting benefits may be attainable. The odd chain fatty acids disclosed herein may be provided with or partial or complete substitution for those complex saccharides that have differential breakdown and uptake. The odd chain fatty acids are provided along with salt constituents, either as salts with the odd chain fatty acids themselves, or in the form of additional salts, e.g., sodium chloride and potassium chloride. The quantity and relative proportion of the salts may be selected to achieve an isotonic liquid without a strong acid taste. Thus, the salt components provide replacement for those essential ions lost in perspiration while, at the same time, yielding a highly palatable beverage.

The beverage of the present invention may be compounded with water and suitably bottled and stored. Alternatively, all the components, save for water, may be prepared in advance as a concentrate for ease of handling and transportation. Also, the beverage may be prepared with carbonated water should such be desirable.

During athletic competition, or other strenuous physical activity, the individual may replace lost body fluids and essential salts while sustaining a high level of energy through consumption of the beverage of the present invention. Moreover, contrary to many of the prior art formulations for such beverages, e.g., extended citrus juices, intake of the beverage of the present invention is not accompanied by a "full" feeling that would present a serious hindrance in athletic competition. Thus, the present dietetic beverage successfully replaces and/or maintains individual body requirements in accordance with the physiological needs thereof and further provides additional storage of energy.

Food Compositions and Additives. The odd chain fatty acids of the present invention may also be formulated into an edible matrix and/or food composition. One such chewable matrix is taught in U.S. Pat. No. 6,723,358 that teachers the encapsulation of edible products, relevant portions incorporated herein by reference. An encapsulated product is obtained by mixing a plasticizer, a ground, free-flowing particulate mixture with the odd chain fatty acids, at least one starch, mixed and heated. A chewable texture is obtained when the starch is maintained substantially ungelatinized. A flavorful product may also be obtained and made part of an overall patient diet without destroying a heat sensitive encapsulant because the oil and starch are heated to develop flavor at high temperatures prior to mixing with a heat sensitive encapsulant. The encapsulated component may be at least one biologically active component, pharmaceutical component, nutraceutical component, or microorganism. The mixture may includes ground cookies that are mixed with the plasticizer, odd chain fatty acids and water to obtain a formable dough or crumbly mass that may be further formed into pieces or pellets and dried to a shelf-stable moisture content.

The present invention will find particular utility in animal feeds. For example, the odd chain fatty acids may be used in conjunction with the feed stocks, e.g., that taught in U.S. Pat. No. 6,777,396, relevant portions incorporated herein by reference. The feed for livestock may include a feed for livestock with additives such as nucleic acids, glutamine and glutamic acid. The feed is provided as part of a method for increasing body weight gain efficiency and feed efficiency in livestock.

The present invention also includes an animal feed composition that includes the odd chain fatty acids. It is contemplated that any odd chain fatty acids may be present in the animal feed in any amount effective to provide nutritive fat to the animal. It is contemplated that the odd chain fatty acids content may vary depending upon the animal or upon the intended nutritive qualities of the feed. Generally, the fat is present in the animal feed in an amount of at least 5%, 10%, 17%, 20%, 25%, 30% or even 40% by weight of the animal feed. It is contemplated that two or more odd chain fatty acids sources may be included in the feed.

The animal feed further includes a solid nutritive source, such as a whole grain, whole wheat, whole rice, whole corn, or whole barley. Alternatively, the solid nutritive source may also include nutritive wheat, nutritive rice, nutritive corn or nutritive barley fraction. Other nutritive sources include those derived from soy, oats, sorghum, and the like. The nutritive source may include other nutritive sources, including sources of carbohydrates (such as molasses solids) that are also provided in liquid form. The solid nutritive source may be present in the animal feed in any suitable amount.

Another nutritive source is a protein source, which may be present in any amount effective to provide protein to the animal. Protein may be present in an amount ranging from about 5% to about 40% by weight of the animal feed. For example, young swine are particularly needy of protein, and protein contents in the upper portion of this range (e.g., a protein content of about 36%) are often used in feeds intended for such swine. For feeds of other animals, the protein is present in an amount ranging from about 10% to about 30% by weight of the animal feed, but more often in an amount ranging from about 15% to about 20% by weight of the animal feed.

Animal feeds may also include a source of fiber source. Sources of fiber may include: soybean hulls, rice hulls, corn hulls, cottonseed, wheat hulls, and the like are considered largely non-nutritive (at least in the case of non-ruminant animals). When the animal feed is intended for use by ruminants, the feed very often includes such fiber source in an amount effective to provide fiber to the animal. Different feed formulas for different animals vary greatly in the amount of fiber desired. The fiber source may be prepared in an amount ranging from about 1% to about 25% by weight of the animal feed, the percentage being expressed by the bulk weight of the hulls or other source.

Pelleted High-Fat Animal Feed. The odd chain fatty acids of the present invention may be incorporated into any of a number of animal feeds. Basic types of animal feeds are taught in, e.g., U.S. Pat. No. 6,746,698, relevant portions incorporated herein by reference, which teaches an animal feed, method for preparing animal feed, and method for feeding an animal. Unlike the present invention, however, the fats taught are standard even chain fatty acids and fats. A master batch of horse feed ration containing full fat corn germ from a corn wet-milling process was formulated in a Hobart mixer. The feed was formulated from the following components:

| | |
|---|---|
| Ground Full-Fat Corn Germ | 24.8% |
| Wheat Midds | 21.1% |
| Ground Whole Corn | 17.9% |
| Soybean Meal | 9.5% |
| Odd Chain Fatty Acid | 25.0% |
| Calcium Carbonate | 1.1% |
| Dicalcium Phosphate | 1.1% |

To an aliquot of the master batch an adhesive may be added, in liquid and/or dry form in an amount sufficient to constitute 5% of the total dry mass of the final pelleted feed. The mixture was then converted into a pelletized horse feed using a pellet mill.

An animal feed was formulated as follows:

| Ingredient | Weight % |
|---|---|
| Corn Germ | 23% |
| Wheat Midds | 21.5% |
| Whole Ground Corn | 15% |
| Soybean Meal | 9% |
| Calcium Carbonate | 1% |
| Dicalcium Phosphate | 1% |
| Odd Chain Fatty Acid | 25.0% |

The ingredients may be combined to form a mixture and the mixture pelletized. In this formulation, the wheat midds were included to provide a source of fiber, the soybean meal was included to provide a source of protein, and the calcium carbonate and dicalcium phosphate were included as mineral calcium sources. The feed may be evaluated for palatability.

A master batch horse ration formula having the following composition was prepared:

| | |
|---|---|
| Full-Fat Corn Germ | 26% |
| Wheat Midds | 21% |
| Ground Corn | 10% |
| Soybean Meal | 6.5% |
| Distillers Dried Grain | 2% |
| Calcium Carbonate | 1% |
| Dried Whole Wheat | 1% |
| Dehydrated Alfalfa | 1% |
| Dicalcium Phosphate | 1% |
| Odd Chain Fatty Acid | 20.0% |

EXAMPLE 5

Use of Odd Chain Fatty Acids to Treat Mitochondrial Fat Oxidation Defects

Other examples of FODs that derive from errors in metabolism include: Carnitine Palmitoyl Transferase I (CPT I) deficiency, Carnitine-Acylcarnitine Translocase (CACT) deficiency, Carnitine Palmitoyl Transferase I (CPT II) deficiency, very long chain acyl-CoA dehydrogenase (VLCAD) deficiency, Trifunctional Protein (TFP) deficiency, long chain acyl 3-hydroxy CoA dehydrogenase (LCHAD) and short chain acyl CoA dehydrogenase (SCAD) deficiency. Patients having each of these diseases were located and placed on an odd chain fatty acid diet, with informed consent and following under IRB. These patients exhibit one or more of the following symptoms: recurrent hypoglycemia (Reye-like); cardiomyopathy: hypertrophic or dilated; hypotonia and/or delayed development; rhabdomyolysis; muscle weakness and fatigue; peripheral neuropathy; retinopathy; seizures and often sudden death due to, e.g., arrhythmias.

The odd chain fatty acid diet and therapy of the present invention was compared to conventional treatments, which include: (1) a low fat, high carbohydrate diet; avoid fasting; frequent or continuous feeding and night time corn starch; or (2) a medium chain triglyceride (MCT oil) for long chain disorders; or (3) insulin and glucose to inhibit lipolysis. However, current treatments fail to treat the hypoglycemia and hepatomegaly (which often persist), the frequency and severity of Rhabdomyolysis; muscle weakness and fatigue are not improved and heart function often remains abnormal. Biochemically, the failure of existing therapies leave patients with impaired Acetyl-CoA production and ketogenesis, there remains an increase Acyl-CoA:CoA (mitochondrion) ratio during illness, a decreased NADH:NAD ratio during illness (mitochondrion), hypoglycemia and hyperammonemia.

TABLE 3

Triheptanoin Patient Demographics.

| FOD | # Patients | Male/Female | Age @ Entry | *Ethnic |
|---|---|---|---|---|
| CPT I | 2 | 1/1 | 4 yr 9 mo-6 yr 11 mo | 2C |
| CACT | 1 | 0/1 | birth | 1H |
| CPT II | 7 | 2/5 | 5 yr 6 mo-51 yrs | 4C, 3J |
| VLCAD | 19 | 9/10 | Neonate-35 yrs | 16C, 1AA, 1ME, 1H |
| LCHAD | 9 | 4/5 | 6 mo-23 yrs | 6C, 2H, 1J |
| TFP | 5 | 5/0 | 32 mo-8 yr 6 mo | 5C |
| "SCAD" | 5 | 5/0 | 19 mo-6 yr 9 mo | 3C, 2J |
| TOTAL: | 48 | | | |

*C = caucasian, H = hispanic, J = jewish, AA = afro-american, ME = middle eastern FIG. 9 is a graph that shows the effects of triheptanoin on patient creatine kinase activity for selected patient populations. Tri-C7 rapidly suppresses CPK levels in long-chain defects because it provides fuel to muscle via 5-carbon ketone bodies, thereby giving propionate and acetate into the CAC, with an increase in energy.

Table 4 summarized a comparison of patent mortality for patients with FOD of conventional treatment (based on the literature, see *Neonatal onset; Conventional Diet Rx: JIMD 22: 488,1999), and the odd chain fatty acids of the present invention. There is a demonstrable increase in patient survival across a number of FODs.

TABLE 4

Patient Mortality Comparison Conventional Diet v. C7 Diet

| Disorder | Conventional Diet (41 patients - 51% withdrawl) | C7 Diet (48 patients - 6% withdrawl) |
|---|---|---|
| CACT* | 5/5 - 100% | 1/1 - 100% (rotavirus) |
| CPT II* | 4/5 - 80% | No patients |
| VLCAD | 6/8 - 75% | 1/19 - 5% |
| TFP | 4/4 - 100% | 1/5 - 0% |
| LCHAD | 2/10 - 20% | 0/9 - 0% |

The following generalized clinical observations demonstrate the effects of the odd chain fatty acids therapy on the patients. First, sudden weight gain was at first welcome and prevented by reduced carbohydrate intake. The use of emulsifiers and recipes that incorporated the odd chain fatty acids into foodstuffs reduced gastrointestinal (GI) intolerance. As regards chronic (occult) infection a vast improvement was noted and rhabdomyolysis was relieved. In a couple of cases a mild toxicity was noted and resolved by the occasional increase in biotin or B12 requirement and was overcome by supplementation in adults, only. Importantly, no "Propionyl Overload" was observed in any patient. Compliance was very good with the minimal withdrawal of 3 (6%) of 51 total patients that withdrew due to complains of GI discomfort and/or weight gain. Most importantly, the vast majority of patients elected to continue beyond protocol: 22 (85%) of 26.

Regarding protein sparing, the following table summarized the results obtained in a patient with Pompe's upon

TABLE 5

Plasma Amino Acids (μM) During Initiation of Anaplerotic Therapy:
"Protein Sparing" in Adult-Onset Glycogen Storage Disease II (Pompe's)

| | Event: | Admit | C7 = 1.0 gm/Kg | | NPO* | | C7 = 1.5 gm/Kg | |
|---|---|---|---|---|---|---|---|---|
| | Time: | Baseline | 13 hrs | 41 hrs | 65 hrs | 84 hrs | 108 hrs | 132 hrs |
| "Oxaloacetate": | | | | | | | | |
| ASPARTATE | (0-10) | 8 | 44 | 112 | 15 | 12 | 50 | 42 |
| "Urea Cycle": | | | | | | | | |
| ORNITHINE | (36-118) | 35 | 78 | 163 | 59 | 50 | 122 | 95 |
| CITRULLINE | (11-51) | 20 | 1 | 43 | 21 | 20 | 35 | 25 |
| ARGININE | (20-122) | 50 | 96 | 93 | 71 | 84 | 102 | 97 |
| "Neurotransmitters": | | | | | | | | |
| **PHENYLALANINE | (35-83) | 62 | 101 | 156 | 69 | 51 | 90 | 84 |
| TYROSINE | (30-100) | 55 | 110 | 62 | 44 | 39 | 56 | 46 |
| **TRYPTOPHAN | (23-86) | 25 | 121 | 43 | 20 | <10 | 40 | 40 |
| Total Amino Acids: | (1540-4415) | 1927 | 3673 | 4160 | 2176 | 2174 | 3568 | 3296 |

*NPO for gastrostomy—IV glucose only;
**Essential amino acids

Table 6 shows the overall Diet Composition; pCO2, and Events during Hospitalization of a Pompe's patient.

| Hospital Day: | 0 | 1 | 4 | 5-6 | 7 | 23 | 33 |
|---|---|---|---|---|---|---|---|
| DIET (% Kcal): | | | | | | | |
| Prot | 29 | 29 | 25 | NPO | 25 | 25 | 25 |
| CHO | 30 | 30 | 27 | | 27 | 24 | 24 |
| Total Lipid | 41 | 41 | 48 | | 48 | 51 | 51 |
| *C7 | 26 | 26 | 35 | | 35 | 40 | 40 |
| Total Kcal: | 1500 | 1500 | 1700 | | 1700 | 1900 | 1900 |
| pCO$_2$ (35-45) | 68 | 43 | 51 | | 42 | 48 | 44 |
| Event: | Admit | | | NPO for PEG | | Extubated | Discharge |

*C7 is included in the "Total Lipid" % Kcal

In conclusion, the odd chain fatty acid diet and therapy of the present invention was found to successfully treat the following FOD disorders: CPT I, CACT, CPT II, VLCAD, TFP, LCHAD and SCAD. The outcome of dietary triheptanoin supplementation included: reduced mortality, cardiomyopathies were resolved and there was a marked attenuation of Rhabdomyolysis. Also, normal glucose homeostasis was observed with the elimination of hepatomegaly. Patients showed improved muscle strength and endurance. In TFP peripheral neuropathy was unchanged and in LCHAD the retinopathy (Choroideremia) was also unchanged.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

In the claims, all transitional phrases such as "comprising," "including," "carrying," "having," "containing," "involving," and the like are to be understood to be open-ended, i.e., to mean including but not limited to. Only the transitional phrases "consisting of" and "consisting essentially of," respectively, shall be closed or semi-closed transitional phrases.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A composition comprising a seven carbon fatty acid source selected from the group consisting of n-heptanoic acid, a triglyceride comprising n-heptanoic acid and triheptanoin, wherein the composition has an acid value of 0.1 or less mg KOH/gr, a hydroxyl value of 2.8 or less mg KOH/gr and wherein the composition is formulated for parenteral, oral, or enteral administration.

2. The composition of claim 1, wherein the seven carbon fatty acid source is heptanoic acid or a triglyceride thereof.

3. The composition of claim 1, wherein the seven carbon fatty acid source is heptanoin, heptanoate, or triheptanoin.

4. The composition of claim 1, wherein the composition is provided in an amount suitable for administration in a range of 1 to 4 grams per kilogram body weight per day.

5. The composition of claim 1, wherein the composition is provided in an amount suitable for administration in a range of 1 to 3 grams per kilogram body weight per day.

6. The composition of claim 1, wherein the composition is provided in an amount suitable for administration in a range of 1 to 2 grams per kilogram body weight per day.

7. The composition of claim 1, wherein the composition is provided in an amount suitable for administration in a range of 0.1 to 2 grams per kilogram body weight per day.

8. The composition of claim 1, wherein the seven carbon fatty acid source is in a dosage unit, wherein the dosage unit comprises at least 15 grams of the seven carbon fatty acid source.

9. The composition of claim 1, wherein the dosage unit comprises 15 to 75 grams of the seven carbon fatty acid source.

10. The composition of claim 1, wherein the dosage unit comprises 75 grams of the seven carbon fatty acid source.

11. The composition of claim 1, wherein the composition is provided in an amount suitable for providing 15% to 40% of the daily dietary calories of a human.

12. The composition of claim 1, wherein the composition is provided in an amount suitable for providing 20% to 35% of the daily dietary calories of a human.

13. The composition of claim 1, wherein the composition is provided in an amount suitable for providing 25% to 35% of the daily dietary calories of a human.

14. The composition of claim 1, wherein the composition is provided in an amount suitable for providing 30% of the daily dietary calories of a human.

15. The composition of claim 1, wherein the composition is provided in an amount suitable for providing 25% of the daily dietary calories of a human.

16. The composition of claim 1, wherein the composition is a nutritional supplement.

17. The composition of claim 1, wherein the composition is a dietary formulation.

18. The composition of claim 1, wherein the composition is a pharmaceutical composition.

19. The composition of claim 1, wherein the composition is administered parenterally.

20. The composition of claim 1, wherein the composition is administered enterally.

21. The composition of claim 1, wherein the composition is administered orally.

22. The composition of claim 1, wherein the composition is provided in an amount suitable for administration in a range of about 1 gram per kilogram body weight per day for an adult for at least 7 or 14 days.

23. The composition of claim 1, wherein the composition is provided in an amount suitable for administration in a range of about 2 to 4 grams per kilogram body weight per day for at least 7 or 14 days.

24. The composition of claim 1, wherein the composition is provided in an amount suitable for administration in a range of about 1 to 2 grams per kilogram body weight per day for at least 7 or 14 days.

25. The composition of claim 1, wherein the dosage unit is at least 25% of the daily fatty acid dose for an adult.

26. The composition of claim 1, wherein the composition is provided in an amount suitable for administration in a range of about 1 to 4 grams per kilogram body weight per day for infants or 0.1 to 2 grams per kilogram body weight per day for adults.

* * * * *